(12) United States Patent
Groll et al.

(10) Patent No.: US 11,561,156 B2
(45) Date of Patent: Jan. 24, 2023

(54) INKJET DEPOSITION OF REAGENTS FOR HISTOLOGICAL SAMPLES

(71) Applicant: Ventana Medical Systems, Inc., Tucson, AZ (US)

(72) Inventors: Henning Groll, Tucson, AZ (US); Melis Hazar, Tucson, AZ (US); Eric L. Klein, Tucson, AZ (US); Raymond T. Kozikowski, III, Tucson, AZ (US); Chana R. Paluszcyk, Tucson, AZ (US); Melinda J. Polaske, Oracle, AZ (US); Raviraj Thakur, West Lafayette, IN (US)

(73) Assignee: Ventana Medical Systems, Inc., Tucson, AZ (US)

( * ) Notice: Subject to any disclaimer, the term of this patent is extended or adjusted under 35 U.S.C. 154(b) by 379 days.

(21) Appl. No.: 15/782,816

(22) Filed: Oct. 12, 2017

(65) Prior Publication Data

US 2018/0052082 A1 Feb. 22, 2018

Related U.S. Application Data

(63) Continuation of application No. PCT/EP2016/058801, filed on Apr. 20, 2016.

(60) Provisional application No. 62/150,122, filed on Apr. 20, 2015.

(51) Int. Cl.
| | |
|---|---|
| *G01N 1/31* | (2006.01) |
| *G01N 33/53* | (2006.01) |
| *G01N 35/10* | (2006.01) |
| *G01N 1/30* | (2006.01) |

(52) U.S. Cl.
CPC ............ *G01N 1/312* (2013.01); *G01N 33/53* (2013.01); *G01N 35/1002* (2013.01); *G01N 35/1011* (2013.01); *G01N 35/1016* (2013.01); *G01N 1/30* (2013.01); *G01N 2001/302* (2013.01);
(Continued)

(58) Field of Classification Search
None
See application file for complete search history.

(56) References Cited

U.S. PATENT DOCUMENTS

| | | | |
|---|---|---|---|
| 4,877,745 A | 10/1989 | Hayes et al. | |
| 4,914,022 A * | 4/1990 | Furmanski | ....... G01N 33/54366 435/40.52 |
| 5,658,802 A | 8/1997 | Hayes et al. | |

(Continued)

FOREIGN PATENT DOCUMENTS

| | | |
|---|---|---|
| JP | 2002-267675 A | 9/2002 |
| JP | 2003004609 A | 1/2003 |

(Continued)

OTHER PUBLICATIONS

International Preliminary Report on Patentability dated Nov. 2, 2017 in corresponding PCT/EP2016/058801 filed Apr. 20, 2016, 13 pages.

(Continued)

*Primary Examiner* — Brian R Gordon
(74) *Attorney, Agent, or Firm* — Charney IP Law LLC; Thomas M. Finetti

(57) ABSTRACT

Devices and methods for the deposition of reagents onto cells or tissue samples are disclosed. Also disclosed are reagent compositions suitable for dispensing via a droplet-on-demand system.

13 Claims, 18 Drawing Sheets
(10 of 18 Drawing Sheet(s) Filed in Color)

(52) U.S. Cl.
CPC ............... *G01N 2001/317* (2013.01); *G01N 2035/1041* (2013.01)

(56) References Cited

U.S. PATENT DOCUMENTS

| | | | |
|---|---|---|---|
| 6,664,044 B1* | 12/2003 | Sato | B01J 19/0046 422/68.1 |
| 6,716,629 B2* | 4/2004 | Hess | B01J 19/0046 435/420 |
| 9,725,613 B2 | 8/2017 | Lopez Garcia et al. | |
| 2002/0176804 A1 | 11/2002 | Strand et al. | |
| 2002/0180475 A1 | 12/2002 | Watanabe | |
| 2002/0192702 A1* | 12/2002 | Kononen | G01N 33/48 435/40.5 |
| 2003/0081209 A1 | 5/2003 | Takahashi et al. | |
| 2003/0143756 A1 | 7/2003 | Fisher et al. | |
| 2004/0136876 A1* | 7/2004 | Fouillet | B01F 15/0216 422/514 |
| 2006/0105453 A1* | 5/2006 | Brenan | B01J 19/0046 435/325 |
| 2008/0090267 A1 | 4/2008 | Komatsu | |
| 2008/0106577 A1 | 5/2008 | Hanaoka et al. | |
| 2010/0128988 A1* | 5/2010 | Kincaid | G06K 9/6253 382/199 |
| 2010/0285573 A1* | 11/2010 | Leck | B01L 3/5088 435/288.4 |
| 2012/0122197 A1 | 5/2012 | Jospeh | |
| 2012/0329143 A1 | 12/2012 | Yamazaki | |
| 2013/0250090 A1 | 9/2013 | Morimoto | |
| 2017/0292899 A1 | 10/2017 | Kasamatsu et al. | |
| 2018/0052082 A1 | 2/2018 | Groll et al. | |
| 2019/0242921 A1 | 8/2019 | Drechsler et al. | |

FOREIGN PATENT DOCUMENTS

| | | |
|---|---|---|
| JP | 2003130866 A | 5/2003 |
| JP | 2007-526479 A | 9/2007 |
| JP | 2008096245 A | 4/2008 |
| JP | 2008/164517 A | 7/2008 |
| JP | 2008185504 A | 8/2008 |
| JP | 2010521678 A | 6/2010 |
| JP | 2013-007688 A | 1/2013 |
| JP | 2015-004552 A | 1/2015 |
| JP | 2015-017258 A | 1/2015 |
| JP | 2015-500983 A | 1/2015 |
| WO | 98/58240 A1 | 12/1998 |
| WO | 0157254 A2 | 8/2001 |
| WO | 2001057254 A2 | 8/2001 |
| WO | 03/072258 A1 | 9/2003 |
| WO | 2004111610 A2 | 12/2004 |
| WO | 2005/084263 A2 | 9/2005 |
| WO | 2006046747 A1 | 5/2006 |
| WO | 2008/112993 A1 | 9/2008 |
| WO | 2011/087841 A1 | 7/2011 |
| WO | 2012/066827 A1 | 5/2012 |
| WO | 2013071357 A2 | 5/2013 |
| WO | 2014/030856 A1 | 2/2014 |
| WO | 2014188029 A1 | 11/2014 |
| WO | 2015086534 A1 | 6/2015 |
| WO | 2016/047625 A1 | 3/2016 |
| WO | 2016170008 A1 | 10/2016 |

OTHER PUBLICATIONS

International Search Report and Written Opinion dated Sep. 1, 2016 in corresponding PCT/EP2016/058801 filed Apr. 20, 2016, 20 pages.
Guo, M.T. et al., Droplet microfluidics for high-throughput biological assays, Lab on a Chip, (2012), pp. 2146-2155, vol. 12.
Puckett, C.A. et al., Fluorescein redirects a ruthenium-octaarginine conjugate to the nucleus, Journal of the American Chemical Society, (2009), pp. 8738-8739, vol. 131 Issue 25.
Sigma, Biofiles_In Vitro, SIGMA, (2008), pp. 1-20, vol. 2.
Slidders, W., A stable iron-hematoxylin solution for staining the chromatin of cell nuclei, Journal of Microscopy, (1969), pp. 61-65, vol. 90, No. 1.
Lovchik et al., Lab Chip, 2012 , pp. 1040-1043.
Lovchik et al., Microfluidic Probe for Advanced Staining of Human Tissue Sections, 15th International Conference on Miniaturized Systems for Chemistry and Life Sciences, Oct. 2-6, 2011, pp. 368-370.
Pepper et al., Thermal Inkjet Printing for Precision Histological Staining, Journal of Histotechnology, 2011, pp. 123-131, vol. 24, No. 3.
Zaugg et al., "Drop-on-Demand Printing of Protein Biochip Arrays," MRS Bulletin/Nov. 2003; www.mrs.org/publications/bulletin.
Risio et al., "Piezoelectric Ink-Jet Printing of Horseradish Peroxidase: Effect of Ink Viscosity Modifiers on Activity," Macromol. Rapid Commun. 2007, 28, 1934-1940, 2007 WILEY-VCH Verlag GmbH & Co. KGaA, Weinheim; DOI: 10.1002/marc.200700226.
Lonini et al., "Dispensing an enzyme-conjugated solution into an ELISA plate by adapting ink-jet printers," J. Biochem. Biophys. Methods 70 (2008) 1180-1184.
Polysciences, Inc. Chemistry Beyond the Ordinary, Hill's Hematoxylin—Specific for Staining Nucleic, Technical Data Sheet 192, Jul. 20, 2015.
Shi, Shan-Rong et al, Antigen Retrieval Immunohistochemistry Based Research and Diagnostics, Visualizing Protein Maps in Tissue, (2010), pp. 369-389, Chapter 21, John Wiley & Sons, Inc.
Biofiles, In Vitro, Medical Microbiology and Read-to-eat Salads; An Interview with Prof. M. Manafi; Issue 2; 2008; Sigma Life Sciences.
Anonymous, Inkjet technology, Wikipedia, (2016), Retrieved from the Internet: URL:https://en.wikipedia.org/w/index.php?title=Inkjet_technology&oldid=718089954,-.
Anonymous, Paraffin wax, Wikipedia, (2016), Retrieved from the Internet: URL:https://en.wikipedia.org/w/index.php?title=Paraffin_wax&direction=prev&oldid=744993819, -.
International Search Report and Written Opinion dated Feb. 21, 2018 in corresponding PCT/EP2017/076558 filed Oct. 18, 2017, pp. 1-16.
Mukai, et al., "Visualizing Protein Maps," Antigen Retrieval Immunohistochemistry Based Research and Diagnostics, Edited by Shan-Rong Shi and Clive R. Taylor Copyright© 2010 John Wiley & Sons, Inc.

* cited by examiner

INKJET DEPOSITION OF REAGENTS FOR HISTOLOGICAL SAMPLES

CROSS REFERENCE TO RELATED APPLICATIONS

This patent application is a continuation of International Patent Application No. PCT/EP2016/058801 filed Apr. 20, 2016, which claims priority to and the benefit of U.S. Provisional Patent Application No. 62/150,122 filed Apr. 20, 2015. Each of these related patent applications is incorporated by reference herein.

BACKGROUND OF THE DISCLOSURE

Molecular pathology is the examination at a molecular level of the DNA, mRNA, and proteins that cause or are otherwise associated with disease. From this examination important information about patient diagnosis, prognosis, and treatment options can be elucidated. Diseases, such as cancer, can be diagnosed by a number of different methods. One method is to identify the presence of a biomarker, such as a cancer biomarker, in tissue or cells, the biomarker being correlated, or thought to be correlated, with a particular cancer type.

Hematoxylin and eosin (H&E) are primary stains that have been used for at least a century and are essential for recognizing various tissue types and the morphologic changes that form the basis of contemporary cancer diagnosis. The stain works well with a variety of fixatives and displays a broad range of cytoplasmic, nuclear, and extracellular matrix features. Hematoxylin has a deep blue-purple color and stains nucleic acids by a complex reaction. Eosin is pink and stains proteins nonspecifically. In a typical tissue, nuclei are stained blue, whereas the cytoplasm and extracellular matrix have varying degrees of pink staining. Well-fixed cells show considerable intranuclear detail. Nuclei show varying cell-type- and cancer-type-specific patterns of condensation of heterochromatin (hematoxylin staining) that are diagnostically very important. Nucleoli stain with eosin. If abundant polyribosomes are present, the cytoplasm will have a distinct blue cast. The Golgi zone can be tentatively identified by the absence of staining in a region next to the nucleus. Thus, the stain discloses abundant structural information, with specific functional implications.

Histochemistry and cytochemistry are techniques often used to identify biomarkers within the context of intact cells by labeling the samples with molecules that bind specifically to the biomarker in a manner that can be visualized on a microscope. Immunohistochemistry (IHC) and immunocytochemistry (ICC) are types of histochemistry and cytochemistry that use antibodies to label the biomarkers. By identifying the biomarker in the context of a tissue environment or cellular environment, spatial relationships between the biomarkers and other morphological or molecular features of the cell or tissue sample can be elucidated, which may reveal information that is not apparent from other molecular or cellular techniques.

These techniques typically require a series of treatment steps conducted on a tissue section (e.g. a tumor biopsy) or cell sample (e.g. blood or bone marrow) mounted on a microscope slide, such as a glass, plastic, or quartz microscope slide. Frequently used steps include pretreatments to prepare the tissue samples for mounting and staining (e.g. deparaffinization, rehydration, and/or and antigen retrieval), labeling of the tissue sample with biomarker-specific antibody or probe, enzyme labeled secondary treatment and incubation, substrate reaction with the enzyme to produce a fluorophore or chromophore highlighting areas of the sample labeled for the biomarker, counterstaining, and the like. Most of these steps are separated by multiple rinse steps to remove unreacted residual reagent from the prior step. Incubations frequently are conducted at elevated temperatures, usually around 37° C., and the tissue must be continuously protected from dehydration.

In view of the large number of repetitive treatment steps needed for IHC, automated systems have been introduced to reduce human labor and the costs and error rate associated therewith, and to introduce uniformity. Examples of automated systems that have been successfully employed include the ES®, NexES®, DISCOVERY™, BENCHMARK™ and Gen II® staining systems available from Ventana Medical Systems (Tucson, Ariz.). These systems employ a microprocessor controlled system including a revolving carousel supporting radially positioned slides. A stepper motor rotates the carousel placing each slide under one of a series of reagent dispensers positioned above the slides. Bar codes on the slides and reagent dispensers permits the computer controlled positioning of the dispensers and slides so that different reagent treatments can be performed for each of the various tissue samples by appropriate programming of the computer.

In order to introduce reagents and other fluids during processing, a reagent delivery system and method is often used. Typically, the regent delivery system automatically pipettes reagents by inserting a needle or plastic tube into the reagent reservoir or vial, drawing up the reagent into the tube with a motor driven syringe, moving the needle to the slide (or other receptacle) and reversing the syringe to dispense the reagent. In a process such as the foregoing, many of the reagents must be deposited on the slide in precisely measured small amounts (as low as the microliter scale).

Instrumentation such as the Ventana Medical Systems ES®, NexES®, BENCHMARK® and DISCOVERY® systems are fundamentally designed to sequentially apply reagents to tissue sections mounted on one by three-inch glass microscope slides under controlled environmental conditions. The instrument must perform several basic functions such as reagent application, washing (to remove a previously applied reagent), jet draining (a technique to reduce the residual buffer volume on a slide subsequent to washing), Liquid Coverslip™ application (a light oil application used to contain reagents and prevent evaporation), and other instrument functions.

The process of staining tissue on a slide consists of the sequential repetition of the basic instrument functions described above. Essentially a reagent is applied to the tissue then incubated for a specified time at a specific temperature. When the incubation time is completed the reagent is washed off the slide and the next reagent is applied, incubated, and washed off, etc., until all of the reagents have been applied and the staining process is complete.

BRIEF SUMMARY OF THE DISCLOSURE

In one aspect of the present disclosure is a primary stain composition comprising a dye (e.g. hematoxylin or eosin), a surfactant, and a viscosity modifier. In some embodiments, the primary stain composition is suitable for dispensing from a droplet-on-demand reagent dispensing system as described further herein. In some embodiments, the droplet-on-demand reagent dispensing system is an inkjet dispensing system. In some embodiments, the primary stain composition further comprises aluminum chloride.

In another aspect of the present disclosure is a primary stain composition comprising a dye, a surfactant, and a viscosity modifier, wherein the composition has a viscosity ranging from about 1 cp to about 40 cp, and a surface tension ranging from about 25 dyne/cm to about 45 dyne/cm. In some embodiments, the composition has a viscosity ranging from about 6 cp to about 10 cp. In some embodiments, the dye is selected from the group consisting of hematoxylin, eosin acridine orange, bismark brown, carmine, coomassie blue, cresyl violet, crystal violet, DAPI ("2-(4-Amidinophenyl)-1H-indole-6-carboxamidine"), ethidium bromide, acid fucsine, Hoechst stains, iodine, malachite green, methyl green, methylene blue, neutral red, nile blue, nile red, osmium tetraoxide, rhodamine, and safranine. In some embodiments, the surfactant is a non-ionic surfactant. In some embodiments, the viscosity modifier is a glycol. In some embodiments, the viscosity modifier is a propylene glycol. In some embodiments, the surfactant is present in an amount ranging from between about 0.01% to about 0.5% by total weight of the primary stain composition. In some embodiments, the viscosity modifier is present in an amount ranging from between about 35% to about 60% by total weight of the primary stain composition. In some embodiments, the primary stain composition further comprises a buffer. In some embodiments, the primary stain composition has a pH ranging from about 2 to about 5. In some embodiments, the primary stain composition has a pH of about 2.2. In some embodiments, the primary stain composition further comprises aluminum chloride.

In some embodiments, the dye is hematoxylin, the surfactant is a non-ionic surfactant, the viscosity modifier is propylene glycol; and the amount of propylene glycol ranges from about 35% to about 60% by total weight of the primary stain composition. In some embodiments, the dye is eosin, the surfactant is a non-ionic surfactant, the viscosity modifier is propylene glycol; and the amount of propylene glycol ranges from about 35% to about 60% by total weight of the primary stain composition.

In another aspect of the present disclosure is a kit comprising a first primary stain composition and a second primary stain composition, wherein the first primary stain composition comprises hematoxylin, a non-ionic surfactant, and propylene glycol, wherein the propylene glycol is present in an amount ranging from about 35% to about 60% by total weight of the first primary stain composition; and wherein the second primary stain composition comprises eosin, a non-ionic surfactant, and propylene glycol, wherein the propylene glycol is present in an amount ranging from about 35% to about 60% by total weight of the second primary stain composition.

In another aspect of the present disclosure is a large molecule reagent composition comprising a biological molecule selected from the group consist of an antibody, an antibody conjugate, an enzyme, and a multimer; a surfactant; and a viscosity modifier; wherein the antibody composition is suitable for dispensing from a droplet-on-demand reagent dispensing system as described further herein. In some embodiments, droplet-on-demand reagent dispensing system is an inkjet dispensing system. In some embodiments, the large molecule reagent composition further comprises aluminum chloride.

In another aspect of the present disclosure is an antibody staining composition comprising an antibody or antibody conjugate, a surfactant, and a viscosity modifier, wherein the antibody composition has a viscosity ranging from about 4 cp to about 11 cp, and a surface tension ranging from about 20 dyne/cm to about 40 dyne/cm. In some embodiments, the antibody staining composition further comprises at least one carrier protein. In some embodiments, at least one carrier protein is selected from the group consisting of bovine serum albumin and normal goat serum. In some embodiments, the surfactant is a non-ionic surfactant. In some embodiments, the surfactant is present in an amount ranging from about 0.01% to about 0.5% by total weight of the antibody staining composition. In some embodiments, the viscosity modifier is glycerol. In some embodiments, the viscosity modifier is present in an amount ranging from about 2% to about 50% by total weight of the antibody staining composition. In some embodiments, the surfactant is a non-ionic surfactant, the viscosity modifier is glycerol or high molecular weight dextran, and wherein the composition further comprises bovine serum albumin; and wherein an amount of glycerol or high molecular weight dextran ranges from about 2% to about 50% by total weight of the antibody staining composition. In some embodiments, the large molecule reagent composition further comprises aluminum chloride.

In another aspect of the present disclosure is a kit comprising a first composition comprising an antibody staining composition and a second component comprising at least one primary stain composition. In some embodiments, the primary stain composition comprises one of hematoxylin or eosin, a non-ionic surfactant, and propylene glycol, wherein the propylene glycol is present in an amount ranging from about 35% to about 60% by total weight of the primary stain composition. In some embodiments, the antibody composition comprises a primary antibody, a surfactant, and a viscosity modifier, wherein the antibody composition has a viscosity ranging from about 4 cp to about 11 cp, and a surface tension ranging from about 20 dyne/cm to about 40 dyne/cm.

In another aspect of the present disclosure is a method of staining a tissue sample comprising (a) positioning a droplet-on-demand print head (e.g. an inkjet print head or other droplet dispensing means) in proximity to (e.g. near, over, or around in x,y,z, space) a portion of the tissue sample to receive a staining reagent, the print head in fluidic communication with a source of the staining reagent; (b) dispensing a predetermined amount the staining reagent from the inkjet print head and onto the portion of the tissue sample at a predetermined velocity. In some embodiments, the method comprises repeating step (b) one or more times. In some embodiments, the method comprises repeating step (b) at least three times. In some embodiments, the method is repeated for different portions of the tissue sample.

In some embodiments, the method further comprises measuring a staining intensity of the dispensed staining reagent. In some embodiments, step (b) is repeated if the measured staining intensity does not meet a predetermined threshold. In some embodiments, the predetermined threshold is an absorbance value of between about 30 AU (arbitrary units) and about 160 AU. In some embodiments, the predetermined threshold is an absorbance value of between about 25 AU and about 60 AU. In some embodiments, the predetermined threshold is an absorbance value of between about 30 AU and about 70 AU. In some embodiments, the predetermined threshold is an absorbance value of between about 44 AU and about 145 AU.

In some embodiments, step (b) is repeated until a cumulative amount of the staining reagent ranges from about 10 $\mu L/in^2$ to about 30 $\mu L/in^2$. In some embodiments, step (b) is repeated until a cumulative amount of the staining reagent ranges from about 12 µL/in² to about 28 µL/in². In some embodiments, step (b) is repeated until a cumulative amount of the staining reagent ranges from about 14 µL/in² to about 28 µL/in².

In some embodiments, the dispensing method replenishes a stain depletion layer in communication with the portion of the tissue sample. In some embodiments, the predetermined velocity is one which allows for the staining reagent to penetrate a puddle in communication with the tissue sample and to replenish a stain depletion layer. In some embodiments, the predetermined velocity is one which allows mixing at an interfacial layer of the tissue sample. In some embodiments, the predetermined velocity ranges from about 5 m/s to about 15 m/s.

In some embodiments, two staining reagents are sequentially applied to the tissue sample. In some embodiments, the staining reagent is a primary stain. In some embodiments, the staining reagent is a composition comprising a dye, a surfactant, and a viscosity modifier, wherein the composition has a viscosity ranging from about 1 cp to about 40 cp and a surface tension ranging from about 25 dyne/cm to about 45 dyne/cm. In some embodiments, the composition is dispensed at a shear rate of between about $1 \times 10^5$ s$^{-1}$ and about $1 \times 10^7$ s$^{-1}$. In some embodiments, one of hematoxylin or eosin is applied first to at least the portion of the tissue sample, and subsequently another of hematoxylin or eosin is applied second to at least the same portion of the tissue sample.

In some embodiments, the staining reagent is a large molecule staining composition. In some embodiments, the large molecule staining composition comprises a large molecule selected from the group consisting of an antibody, an antibody conjugate, a multimer, and an enzyme; a surfactant; and a viscosity modifier, wherein the composition has a viscosity ranging from about 4 cp to about 11 cp, and a surface tension ranging from about 20 dyne/cm to about 40 dyne/cm. In some embodiments, the large molecule staining composition is dispensed at a shear rate of less than about $5 \times 10^5$ s$^{-1}$.

In some embodiments, the method further comprises the step of optionally depositing one or more additional reagents prior to or after each dispensing step, wherein the one or more additional reagents are selected from the group consisting of deparaffinization agents, washes, rinses, diluents, buffers, or detection reagents. In some embodiments, the step of optionally depositing one or more reagents is performed by dispensing the one or more reagents from an inkjet print head. In some embodiments, the step of optionally depositing one or more reagents is performed by another deposition means.

In another aspect of the present disclosure is a method of dispensing reagent onto a biological sample comprising: overlaying a protective fluid layer onto a biological sample, the biological sample disposed on a support medium; dispensing reagent droplets of between about 1 pL to about 50 pL such that the reagent droplets penetrate the protective fluid layer and contact the biological sample; wherein the reagent droplets comprise a reagent composition selected from the group consisting of a primary stain reagent composition and an antibody reagent composition. In some embodiments, the reagent droplets are dispensed at a velocity of between about 5 m/s to about 15 m/s. In some embodiments, the protective fluid layer is an aqueous puddle. In some embodiments, the protective fluid layer is an immiscible oil. In some embodiments, a density of the reagent droplets is greater than a density of the immiscible oil. In some embodiments, a kinetic energy of the reagent droplets is greater than a surface tension of the immiscible oil. In some embodiments, a kinetic energy of the reagent droplets is greater than a surface tension of the protective fluid layer. In some embodiments, the kinetic energy is greater than $9.52 \times 10^{-10}$ Joules.

In some embodiments, the primary stain reagent composition comprises a dye, a surfactant, and a viscosity modifier, wherein the composition has a viscosity ranging from about 1 cp to about 40 cp and a surface tension ranging from about 25 dyne/cm to about 45 dyne/cm. In some embodiments, the primary stain reagent composition is dispensed at a shear rate of between about $1 \times 10^5$ s$^{-1}$ and about $1 \times 10^7$ s$^{-1}$. In some embodiments, the antibody reagent composition comprising a primary antibody, a surfactant, and a viscosity modifier, wherein the composition has a viscosity ranging from about 4 cp to about 7 cp, and a surface tension ranging from about 20 dyne/cm to about 40 dyne/cm. In some embodiments, the antibody composition is dispensed at a shear rate of less than about $5 \times 10^5$ s$^{-1}$.

In another aspect of the present disclosure is a method of dispensing reagent onto a biological sample comprising: overlaying a protective fluid layer onto a biological sample, the biological sample disposed on a support medium; dispensing a pH modifier to the biological sample; and dispensing reagent droplets at a velocity of between about 5 m/s to about 15 m/s; wherein the reagent droplets comprise a reagent composition selected from the group consisting of a primary stain reagent composition and an antibody reagent composition. In some embodiments, an amount of reagent droplets dispensed ranges from about 10 µL/in² to about 30 µL/in². In some embodiments, the pH modifier has a pH ranging from about 3 to about 5. In some embodiments, the protective fluid layer is an immiscible oil and wherein a kinetic energy of the reagent droplets is greater than a surface tension of the immiscible oil. In some embodiments, the primary stain reagent composition comprises a dye, a surfactant, and a viscosity modifier, wherein the composition has a viscosity ranging from about 1 cp to about 40 cp and a surface tension ranging from about 25 dyne/cm to about 45 dyne/cm. In some embodiments, primary stain reagent composition is dispensed at a shear rate of between about $1 \times 10^5$ s$^{-1}$ and about $1 \times 10^7$ s$^{-1}$. In some embodiments, an antibody reagent composition comprising a primary antibody, a surfactant, and a viscosity modifier, wherein the composition has a viscosity ranging from about 4 cp to about 7 cp, and a surface tension ranging from about 20 dyne/cm to about 40 dyne/cm. In some embodiments, the antibody composition is dispensed at a shear rate of less than about $5 \times 10^5$ s$^{-1}$.

In another aspect of the present disclosure is a method of dispensing reagent onto a biological sample comprising: overlaying a protective fluid layer onto a biological sample, the biological sample disposed on a support medium; dispensing reagent droplets with a kinetic energy sufficient to penetrate the protective fluid layer for the reagent droplets to reach the biological sample and such that a spatial density of reagent droplets deposited on the biological sample ranges from about 50 dpi to about 1200 dpi, wherein the reagent droplets comprise a reagent composition selected from the group consisting of a primary stain reagent composition and a large molecule staining composition. In some embodiments, the protective fluid layer is an immiscible oil and wherein a density of the reagent droplets is greater than a density of the immiscible oil. In some embodiments, the large molecule staining composition comprises a large molecule selected from the group consisting of an antibody, an antibody conjugate, a multimer, and an enzyme; a surfactant;

and a viscosity modifier, wherein the composition has a viscosity ranging from about 4 cp to about 7 cp, and a surface tension ranging from about 20 dyne/cm to about 40 dyne/cm. In some embodiments, the large molecule staining composition is dispensed at a shear rate of less than about $5 \times 10^5$ s$^{-1}$. In some embodiments, the primary stain reagent composition comprises a dye, a surfactant, and a viscosity modifier, wherein the composition has a viscosity ranging from about 1 cp to about 40 cp and a surface tension ranging from about 25 dyne/cm to about 45 dyne/cm. In some embodiments, the primary stain reagent composition is dispensed at a shear rate of between about $1 \times 10^5$ s$^{-1}$ and about $1 \times 10^7$ s$^{-1}$.

In another aspect of the present disclosure is a method of dispensing one or more reagents onto a biological sample, the method comprising overlaying a protective fluid layer onto a biological sample, the biological sample disposed on a support medium (e.g. a microscope slide); dispensing reagent droplets via a droplet-on-demand system such that the reagent droplets penetrate the protective fluid layer and contact the biological sample; wherein the reagent is selected from the group consisting of a primary stain reagent composition or a large molecule reagent reagent composition. In some embodiments, the primary stain composition comprises a dye, a surfactant, and a viscosity modifier, wherein the composition has a viscosity ranging from about 1 cp to about 40 cp and a surface tension ranging from about 25 dyne/cm to about 45 dyne/cm. In some embodiments, the dye is hematoxylin, the surfactant is a non-ionic surfactant, the viscosity modifier is propylene glycol; and wherein an amount of propylene glycol ranges from about 35% to about 60% by total weight of the primary stain composition. In some embodiments, the dye is eosin, the surfactant is a non-ionic surfactant, the viscosity modifier is propylene glycol; and wherein an amount of propylene glycol ranges from about 35% to about 60% by total weight of the primary stain composition. In some embodiments, the large molecule reagent staining composition comprises a primary antibody, a surfactant, and a viscosity modifier, wherein the composition has a viscosity ranging from about 4 cp to about 7 cp, and a surface tension ranging from about 20 dyne/cm to about 40 dyne/cm. In some embodiments, the protective fluid layer is an aqueous puddle. In some embodiments, the reagent droplets are provided with a velocity sufficient to penetrate and replenish a depletion layer around the biological sample. In some embodiments, the reagent droplets are dispensed at a velocity of between about 5 m/s to about 15 m/s. In some embodiments, the protective fluid layer is an immiscible fluid, e.g. an oil. In some embodiments, a density of the reagent droplets is greater than a density of the immiscible oil. In some embodiments, a kinetic energy of the reagent droplets is greater than a surface tension of the immiscible oil. In some embodiments, a Weber number of the reagent droplets is less than about 18. In some embodiments, the primary stain reagent solution is dispensed at a shear rate of between about $1 \times 10^5$ s$^{-1}$ and about $1 \times 10^7$ s$^{-1}$ and the antibody reagent solution is dispensed at a shear rate of less than about $5 \times 10^5$ s$^{-1}$.

In another aspect of the present disclosure is a means for dispensing a primary staining reagent composition or a large molecule reagent staining composition to a tissue sample, wherein a volume of the primary staining reagent composition or the large molecule reagent staining composition dispensed ranges from about 10 µL/in$^2$ to about 30 µL/in$^2$. In some embodiments, the dispensing means is an inkjet print head. In some embodiments, the dispensing means is a droplet-on-demand system, comprising a target imaging system, a relative motion system, a print head, a fluid reservoir, and a pressure control means. In some embodiments, the dispensing means further comprises a print head cleaning system. In some embodiments, the dispensing means is as illustrated in FIG. 1A. In some embodiments, the primary staining reagent composition and the large molecule reagent staining composition are formulated to have a viscosity suitable for dispensing with the dispensing means.

In another aspect of the present disclosure is an automated slide staining apparatus comprising (a) a dispenser for dispensing reagent droplets having a volume ranging from about 1 pL to about 50 pL; (b) a slide support adapted to hold a microscope slide; (c) at least one reagent reservoir comprising a primary stain reagent composition or a large molecule stain composition, the reservoir in fluid communication with the inkjet printing head; and (d) a control module containing a processor and memory, wherein the control module is programmed to direct the inkjet printing head to dispense the composition onto a microscope slide held by the slide support.

In another aspect of the present disclosure is a computer implemented method comprising the steps of (i) imaging a first portion of a slide, the slide containing a tissue sample; (ii) selecting a second portion of the slide for application of a staining reagent, wherein the second portion is a subset of the first portion; (iii) depositing a staining reagent to the second portion via an inkjet deposition system over a plurality of passes. In some embodiments, between about 360 nL/in$^2$ to about 14.4 µL/in$^2$ of staining reagent is deposited to the second portion per pass of the deposition system.

In another aspect of the present disclosure is a computer system for staining a tissue sample comprising one or more processors and at least one memory, the at least one memory storing non-transitory computer-readable instructions for execution by the one or more processors to cause a staining apparatus, having a droplet-on-demand dispensing mechanism, in communication with the computer system to dispense a predetermined quantity of a primary staining reagent composition or a large molecule reagent composition onto at least a portion of a biological sample.

It would be advantageous to apply or dispense reagents with more precision (e.g. dosing precision, temporal precision, in situ mixing) as compared with conventional staining methods. It would also be advantageous to dispense reagents with less reagent volume (and hence less waste), and/or to drive staining kinetics at higher rates, again as compared with conventional staining methods. Applicants have found that dispensing of reagent solutions via a droplet-on-demand technology (e.g. inkjet technology or piezoelectric technology) enables consistent results, and is suitable for incorporation within automated staining processes. Applicants have also discovered that a staining intensity may be optimized (e.g. "dialed-in") by dispensing more or less reagent mass onto the tissue via a droplet-on-demand system. Indeed, Applicants have found that reagent mass may be varied by one of several methods including (i) applying reagent by multiple passes of a dispensing mechanism; (ii) varying the dots per inch (dpi) of reagent dispensing; (iii) varying the droplet volume; and/or (iv) varying the reagent concentration, as disclosed herein. Applicants have unexpectedly discovered that the staining reaction kinetics appear to be faster than with prior art puddle technology, as discussed further herein. Applicants have also found that dispensing reagent solutions via a droplet-on-demand deposition process allows for a significant reduction in reagent usage, again while providing the same staining intensities as compared with conventional staining methods. These and other comparatively superior results are described further herein.

BRIEF DESCRIPTION OF THE FIGURES

The patent or application file contains at least one drawing executed in color. Copies of this patent or patent application publication with color drawings will be provided to the Office upon request and the payment of the necessary fee.

DETAILED DESCRIPTION

Figure 1A:
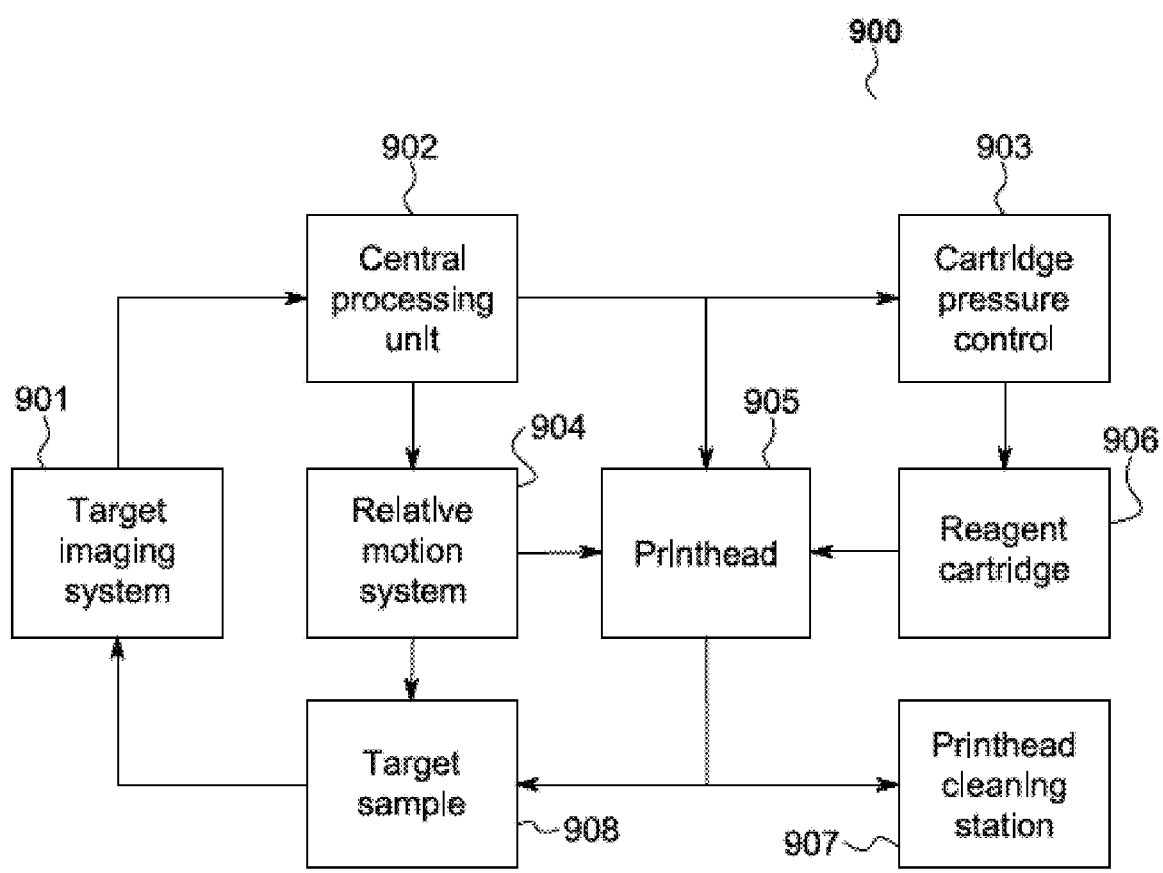
FIG. 1A sets forth a droplet-on-demand system according to embodiments of the present disclosure.

In general, the present disclosure is directed to the delivery or dispensing of one or more reagents to a biological sample utilizing droplet-on-demand technology. Once dispensed, the reagent is distributed to the cells, cell membranes, nuclei and/or tissue or structures contained within the biological sample. The presently disclosed method is uniquely characterized by the ability to deposit reagents for staining reactions with (i) spatial selectivity both within a sample and on a slide; (ii) the ability to print films onto the sample with reagent film thicknesses down to the size scale of a tissue section (approximately 4 µm in height) which is smaller than the thickness of any diffusion depletion layers that exist in staining puddles; and (iii) the ability to stain regions of interest on the sample down to the size scale of single droplets, as defined by the particular droplet generation technology utilized. For example, in some embodiments, the minimum staining region is an area of tissue approximately 25-60 µm in diameter. As will be described in further detail herein, the reagent dispensed include a primary stain or an antibody useful in histochemistry, such that targets within the biological sample may be stained, detected and analyzed.

As used herein, the singular terms "a," "an," and "the" include plural referents unless the context clearly indicates otherwise. Similarly, the word "or" is intended to include "and" unless the context clearly indicates otherwise.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein, the term "antibody," refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments (such as F(ab')2 fragments, Fab' fragments, Fab'-SH fragments and Fab fragments as are known in the art, recombinant antibody fragments (such as sFv fragments, dsFv fragments, bispecific sFv fragments, bispecific dsFv fragments, F(ab)'2 fragments, single chain Fv proteins ("scFv"), disulfide stabilized Fv proteins ("dsFv"), diabodies, and triabodies (as are known in the art), and camelid antibodies) that specifically bind to a molecule of interest (or a group of highly similar molecules of interest) to the substantial exclusion of binding to other molecules. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins.

A "biological sample" or "tissue sample" can be any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer) which are suitable for histochemical or cytochemical analysis, such as samples that preserve the morphological characteristics of the cells and/or tissues to be analyzed. For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In certain examples, a sample is a quality control sample. In other examples, a sample is a test sample. For example, a test sample is a cell, a tissue or cell pellet section prepared from a biological sample obtained from a subject. In an example, the subject is one that is at risk or has acquired. Samples can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Samples can include multiple targets that can be specifically bound by one or more detection probes.

As used herein, the phrase "dip and dunk" refers to a staining technology whereby the sample and microscope slide are submerged into a path of staining reagent for each assay step.

As used herein, the terms "drop-on-demand," "droplet-on-demand", or "droplet-based" (and other like terms or phrases) refer to a staining technology that deposits discrete droplets of reagent onto the target sample, as opposed to "flooding" the slide or sample thereon with reagent. In some embodiments, the droplet-on-demand technology utilizes inkjet technology or piezoelectric technology. In some embodiments disclosed herein, the droplet dispensing technology is facilitated using an inkjet print head or like technology.

As used herein, the term "humectant" refers to a hygroscopic substance used to keep a substance, e.g. a tissue sample, moist; it is the opposite of a desiccant. It is often a molecule with several hydrophilic groups, most often hydroxyl groups; however, amines and carboxyl groups, sometimes esterified, can be encountered as well (its affinity to form hydrogen bonds with molecules of water is the crucial trait). It is believed that a humectant attracts and retains the moisture in the air nearby via absorption, drawing the water vapor into and/or beneath the organism/object's surface. By contrast, desiccants also attract ambient moisture, but adsorb—not absorb—it, by condensing the water vapor onto the surface, as a layer of film. In the context of inkjet deposition or like technologies, a humectant may be important for maintaining a viable nozzle. In some embodiments, it is important for keeping the tissue sample or biological sample hydrated during thin film processing.

The term "inkjet" in this disclosure refers to the family of drop-on-demand technologies where a piezoelectric (or thermal) element is used to actuate a droplet from a dispense manifold. This may include direct and non-contact methods common to the commercial printing industry or those used outside of the commercial printing industry.

As used herein, the term "immunohistochemistry" refers to a method of determining the presence or distribution of an antigen in a sample by detecting interaction of the antigen with a specific binding agent, such as an antibody. A sample is contacted with an antibody under conditions permitting antibody-antigen binding. Antibody-antigen binding can be detected by means of a detectable label conjugated to the antibody (direct detection) or by means of a detectable label conjugated to a secondary antibody, which binds specifically to the primary antibody (indirect detection).

As used herein, the term "microfluidic" refers to a staining technology requiring an opposable surface to the glass microscope slide and a means for a flow-based introduction and evacuation of staining reagents into the gap. Further, a desired gap height should be created such that the flow of reagent across the surface of the slide is laminar and the total volume inside of the gap is minimized.

As used herein, the term "primary antibody" refers to an antibody which binds specifically to a target protein antigen in a tissue sample. A primary antibody is generally the first antibody used in an immunohistochemical procedure. Primary antibodies also include those antibodies conjugated to another molecule (e.g. a label, hapten, etc.). Primary antibodies may serve as "detection probes" for detecting a target within a tissue sample.

As used herein, the term "primary stain" is a dye or like molecule that enhances contrast in a tissue sample. In some embodiments, the primary stain is one which directly "labels" a biological structure within or on a cell, without the employment of a specific binding agent, such as an antibody. Some examples of primary stains include hematoxylin and eosin. Other examples of primary stains include acridine orange, bismark brown, carmine, coomassie blue, cresyl violet, crystal violet, DAPI ("2-(4-Amidinophenyl)-1H-indole-6-carboxamidine"), Ethidium bromide, acid fucsine, Hoechst stains (Hoechst 33342 and Hoechst 33258, which are a bis-benzimidazole derivatives), iodine, malachite green, methyl green, methylene blue, neutral red, nile blue, nile red, osmium tetraoxide, rhodamine, and safranin. Other examples of primary stains include those stain used to stain bacteria (Gram-positive or Gram-negative stains), stains used to identify endospores (endospore staining), stains used to help identify species of Mycobacterium tuberculosis (Ziehl-Neelsen stain), Papanicolaou staining kits (which use a combination of haematoxylin, Orange G, eosin Y, Light Green SF yellowish, and sometimes Bismarck Brown Y), Periodic acid-Schiff stains ("PAS stains"), silver stains, etc. Yet other non-limiting primary stains include (i) histologic stains to selectively demonstrate Mycobacterium and other acid fast organisms or components (e.g. the AFB III Staining Kit, available from Ventana Medical Systems, Tucson, Ariz.); (ii) histologic stains to differentiate acid mucin from neutral polysaccharides (e.g. the Alcian Blue for PAS, also available from Ventana); (iii) histologic stain sto demonstrate weakly acidic mucopolysaccharide (e.g. Alcian Blue Staining Kit, also available from Ventana); (iv) histologic stains for *Helicobacter pylori* (e.g. Alcian Yellow Staining Kit, also available from Ventana); (v) histologic stains to selectively demonstrate amyloid (e.g. Congro Red Staining Kit, also available from Ventana); (vi) histologic stains to differentiate acid mucin from neutral polysaccharides (e.g. Diastase Kit, also available from Ventana); (vii) histologic stains to demonstrate elastic fibers in tissue sections (e.g. Elastic Staining Kit, also available from Ventana); (viii) histologic stains to differentiate leukocytes in bone marrow and other hematopoietic tissue (lymph nodes) (e.g. Giemsa Staining Kit, also available from Ventana); (ix) histologic stains to demonstrate polysaccharides in the cell walls of fungi and other opportunistic organisms, including, but not limited to, stains able to distinguish pathogenic fungi such as *Aspergillus* and *Blastomyces*1 and other opportunistic organisms such as *Pneumocystis carinii* (e.g. GMS II Staining Kit, also available from Ventana); (x) histologic stains to demonstrate gram-negative and gram-positive bacteria (e.g. Gram Staining Kit, also available from Ventana); (xi) histologic stains used to study connective tissue, muscle and collagen fibers (e.g. Green for Trichrome, also available from Ventana); (xii) histologic stains to detect iron pigment in bone marrow, tissue with hemochromatosis, and hemosiderosis (e.g. Iron Staining Kit, also available from Ventana); (xiii) histologic stains to demonstrate capillary basement membrane (e.g. Jones H&E Staining Kit or Jones Light Green Staining kit, both also available from Ventana); (xiv) histologic stains for detection of fungus (e.g. Light Green for PAS, also available from Ventana); (xv) histologic stains to detect acid mucopolysaccharides (mucin) (e.g. Muciarmine Staining Kit, also available from Ventana); (xvi) histologic stains used to demonstrate the presence of glycogen, including stains that may assist in the identification of positive reticular fibers, basement membrane, fungus, and neutral mucopolysaccharides, or those stains that may aid in distinguishing a PAS positive secreting adenocarcinoma from an undifferentiated PAS negative squamous cell carcinoma (e.g. PAS Staining Kit, also available from Ventana); (xvii) histologic stains to demonstrate reticular fiber (e.g. Reticulum II Staining Kit, also available from Ventana); (xviii) histologic stains used to study specific argyrophilic microorganisms (e.g. Steiner II Staining Kit, also available from Ventana); (xix) histologic silver stains to aide in the identification of the causative organisms of diseases such as some gastric ulcers (*H. pylori*), Lyme disease, Legionnaire's disease, cat scratch fever, etc. (e.g. Steiner Staining Kit, also available from Ventana); (xx) histologic stains to study connective tissue, muscle and collagen fibers (e.g. Trichrome II Blue Staining Kit, also available from Ventana); (xxi) histologic stains to study connective tissue, muscle and collagen fibers (e.g. Trichrome Staining Kit, Trichrome III Blue Staining Kit, or Trichrome III Green Staining Kit, each also available from Ventana). The skilled artisan will also recognize that there exist other primary stains, or for that matter dyes, that may be used in conjunction with the kits, methods, and compositions (e.g. primary stain compositions, reagent compositions) of the present disclosure.

As used herein, the term "puddle" refers to a single-slide staining technology whereby the entire sample area surface of the microscope slide is covered in a volume of reagent for each assay step.

As used herein, the term "reagent" may refer to any fluid deposited onto a tissue section or cytology sample, that is used in the context of a morphological (e.g. hematoxylin and eosin), immunohistochemical, or special stain. This includes, but is not limited to, oils, organics, and bridging reagents for removing wax (i.e. deparaffinization); washes, rinses, diluents, or buffers used to set reaction conditions, dilute reagents to an appropriate concentration, quench reactions, or wash away excess reactants; small molecule dyes used for morphological staining and special stains; antibodies, antibody conjugates, enzymes, multimers, amplifiers, chromogenic substrates, fluorescent detection chemistries, chemiluminescent substrates, and enzyme-reaction co-factors, used in IHC or ICC staining.

As used herein, "surfactants" are classified as anionic, cationic, or nonionic, depending on their mode of chemical action. In general, surfactants reduce interfacial tension between two liquids. A surfactant molecule typically has a polar or ionic "head" and a nonpolar hydrocarbon "tail." Upon dissolution in water, the surfactant molecules aggregate and form micelles, in which the nonpolar tails are oriented inward and the polar or ionic heads are oriented outward toward the aqueous environment. The nonpolar tails create a nonpolar "pocket" within the micelle. Nonpolar compounds in the solution are sequestered in the pockets formed by the surfactant molecules, thus allowing the nonpolar compounds to remain mixed within the aqueous solution. In some embodiments, the surfactant may be used to produce uniform spreading of reagents across a tissue section as well as decrease background staining.

As used herein, a "target" may be a particular tissue in a biological sample or a particular molecule or marker in a biological sample. Examples of the target include antigens (including haptens), antibodies, and enzymes. Further examples of targets include, generally, proteins, peptides, nucleic acids, sugars, and lipids. The reagents for use in the present disclosure may be those that are capable of converting the target materials present in the biological sample into detectable forms so that the localization of the targets can be detected (such as visually).

Droplet-on-Demand Dispensing System and Methods of Dispensing Reagents

In one aspect of the present disclosure is a device or system for the deposition of one or more reagents onto biological samples comprising a reagent deposition system utilizing droplet-on-demand technology, e.g. an inkjet dispensing system. According to the present disclosure, the reagent, or composition comprising the reagent, is delivered onto the biological sample, or a region or portion thereof, in the form of droplets to effect spotting or staining of the sample with the reagent solution. Droplet-on-demand technology, including piezoelectric or inkjet dispensing technology, is described further in, for example, U.S. Pat. No. 4,877,745 and in PCT Publication No. WO98/47006, the disclosures of which are hereby incorporated by reference herein in their entireties.

The elements of a droplet-on-demand staining system 900 according to some embodiments of the present disclosure are set forth in FIG. 1A. FIG. 1A illustrates the print head 905 and its relationship with the target sample 908 (the target sample may be a biological samples or tissue sample mounted on a standard microscope slide). To create a "staining job," the target sample 908, in some embodiments, may be analyzed by a target imaging system 901 to determine the spatial position of the target sample. This information is then subsequently fed into the central processing unit 902, which interprets the imaging information and the assay, and then subsequently sends instructions including, for example, timing and coordination information, to the print head 905, a pressure control system 903, and a relative motion system 904. The relative motion system 904 is designed to position the print head 905 and/or target sample 908 into alignment to initiate dispensing of staining droplets (e.g. reagent staining droplets) onto the sample. In some embodiments, fluid or reagent is fed from the reagent cartridge 906 to the print head 905 and onto the target sample 908. The relative motion system 904 is coordinated with the dispense timing from the print head 905 via a central processing unit 902 to produce the desired stain image, as defined by the image provided in 901 and interpreted by 902. Periodically, cleaning of a print head is required, per the print head cleaning station 907. Element 907 interacts directly with the print head to actively clean and force fluid through the print nozzles, priming the nozzles for staining. In some embodiments, a small positive pressure, e.g. about 10 psi or less, may be applied to the cartridge in order to actively clear fluid from the nozzles.

The skilled artisan will appreciate that the droplet-on-demand staining system 900 may be communicatively coupled to additional components, e.g. analyzers, scanners, computer systems, etc. (see FIG. 1B). In general, droplet-on-demand staining system 900 can include, without limitation, a target imaging system 901 having one or more image capture devices. Image capture devices can include, without limitation, a camera (e.g., an analog camera, a digital camera, etc.), optics (e.g., one or more lenses, sensor focus lens groups, microscope objectives, etc.), imaging sensors (e.g., a charge-coupled device (CCD), a complimentary metal-oxide semiconductor (CMOS) image sensor, or the like), photographic film, or the like. In digital embodiments, the image capture device can include a plurality of lenses that cooperate to prove on-the-fly focusing. A CCD sensor can capture a digital image of the specimen. One method of producing a digital image includes determining a scan area comprising a region of the microscope slide that includes at least a portion of the specimen. The scan area may be divided into a plurality of "snapshots." An image can be produced by combining the individual "snapshots." In some embodiments, the target imaging system 901 produces a high-resolution image of the entire specimen, one example for such an apparatus being the VENTANA iScan HT slide scanner from Ventana Medical Systems, Inc. (Tucson, Ariz.), and may be communicatively coupled to the system 900.

Figure 1B:
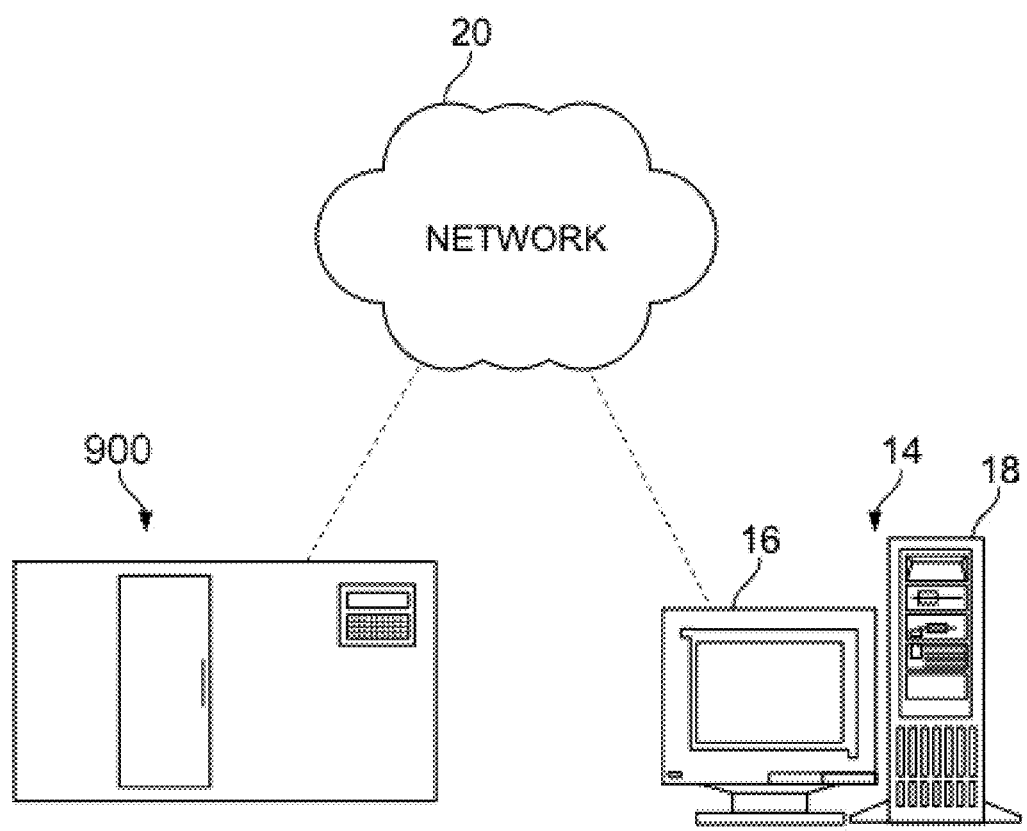
FIG. 1B sets forth a system, which may comprise or be tied to a droplet-on-demand system according to embodiments of the present disclosure.

With reference to FIG. 1B, the computer device 14 may include a central processing unit (which may be CPU 902 or may be a separate CPU), and computer device 14 may include a desktop computer, a laptop computer, a tablet, or the like and can include digital electronic circuitry, firmware, hardware, memory, a computer storage medium, a computer program, a processor (including a programmed processor), or the like. The illustrated computing system 14 of FIG. 1B is a desktop computer with a screen 16 and a tower 18. The tower 18 can store digital images in binary form from the target imaging system 901. In some embodiments, a network 20 or a direct connection interconnects the droplet-on-demand staining system 900 and the computer system 14. The computer systems include one or more processors that are programmed with a series of computer-executable instructions, the instructions being stored in a memory.

The skilled artisan will appreciate that the droplet-on-demand components may be part of a larger system comprising additional components useful in preparing, processing, and/or analyzing biological samples. For example, the droplet-on-demand system 900 of the present disclosure may be tied to a specimen processing apparatus (either upstream or downstream from system 900) that can perform one or more preparation processes on the tissue specimen. The preparation process can include, without limitation, deparaffinizing a specimen, conditioning a specimen (e.g., cell conditioning), staining a specimen, performing antigen retrieval, etc. The skilled artisan will also appreciate that even though the droplet-on-demand dispensing system of the preset disclosure provides a means for staining a sample (e.g. primary stains or IHC stains), the system may be coupled with other staining systems, such as those for performing immunohistochemistry staining (including labeling) and/or performing in situ hybridization (e.g., SISH, FISH, etc.) staining (including labeling), as well as other processes for preparing specimens for microscopy, microanalyses, mass spectrometric methods, or other analytical methods.

Figure 2:
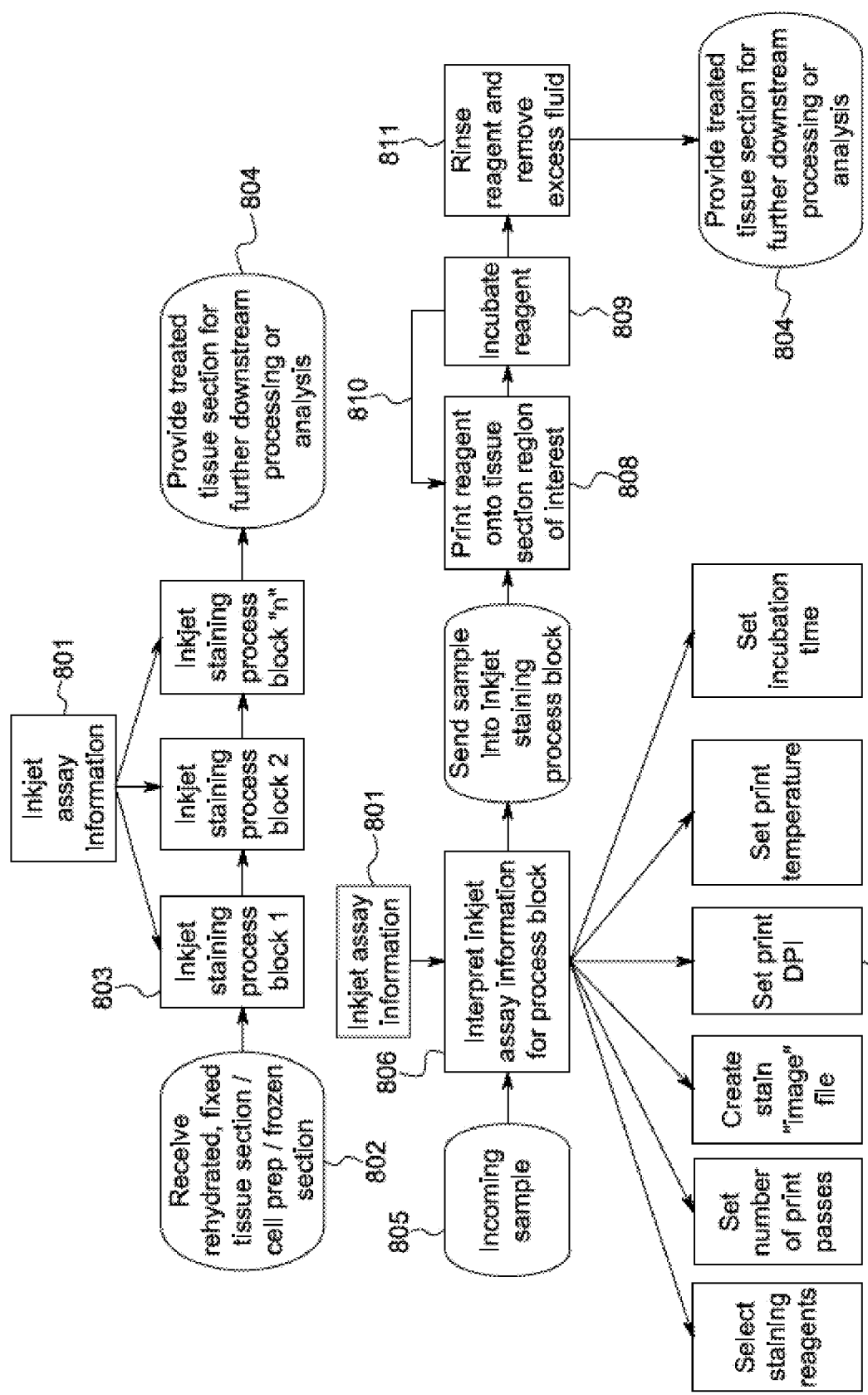
FIG. 2 sets forth a reagent dispensing process according to one embodiment of the present disclosure.

FIG. 2 sets forth a process utilizing droplet-on-demand technology as part of an automated staining system. While FIG. 2 illustrates a process map in the context of inkjet dispensing technology, the skilled artisan will recognize that the system may utilize other droplet-on-demand technologies as known to those of ordinary skill in the art. With reference to FIG. 2, the biological sample is first introduced 802. In some embodiments, the biological sample may include a deparaffinized tissue section, a frozen tissue section, or a cell sample. In some embodiments, the droplet-on-demand dispensing system may include dispensing reagents for the deparaffinization of tissue sections (or deparaffinization may occur alternatively in an upstream process). The necessary assay information 801 for the incoming sample is converted into process steps and/or parameters and then partitioned into "inkjet staining blocks" 803 that may be uniquely defined by hardware configurations or defined by software instructions for the hardware defining different process blocks. The process blocks 803 may be spatially separated within a system or may exist as a monolithic architecture capable of reconfiguring for each of these blocks. The complete assay is defined as the sequential execution of 803 process blocks with the outcome of a transformed sample ready for further downstream processing 804.

FIG. 2 also provides an expanded view of one embodiment of an inkjet staining process block 803. In some embodiments, the incoming sample is defined as in 802 but with optional additional inkjet or droplet-based processing operations performed on the sample prior to introduction to the inkjet staining process block. Block 806 defines the front-end processing step where the inputs of inkjet assay information 801 and the sample 805 are synthesized and partitioned into parameter settings that define the inkjet staining operation to be performed in that process block. In some embodiments, parameters 807 to be set at this step of the process include (i) the particular staining reagent to be dispensed; (ii) the number of print passes to be performed over the sample; (iii) the staining area in the context of a print image file which may print (a) an entire microscope slide, (b) only the regions on the slide having tissue samples, or (c) some combination of sample area and glass regions, multiple tissue samples, or multiple regions within a single sample; (iv) the print DPI, defining the density of droplets to dispense onto the target; (v) the temperature conditions of the process block; and (vi) the incubation times and routine required for the process block. Once the process block is defined, the sample is introduced into the block for execution of the inkjet staining process, as defined at 808, 809, and 810. These three steps generally represent the active portion of dispensing and/or the reaction of the reagents with the sample (see also FIGS. 7 and 8A). Finally, at 811 any remaining unreacted printed reagent is washed away and the excess fluid on the slide is removed resulting in a transformed sample ready for further downstream processing at 804.

Figure 3:
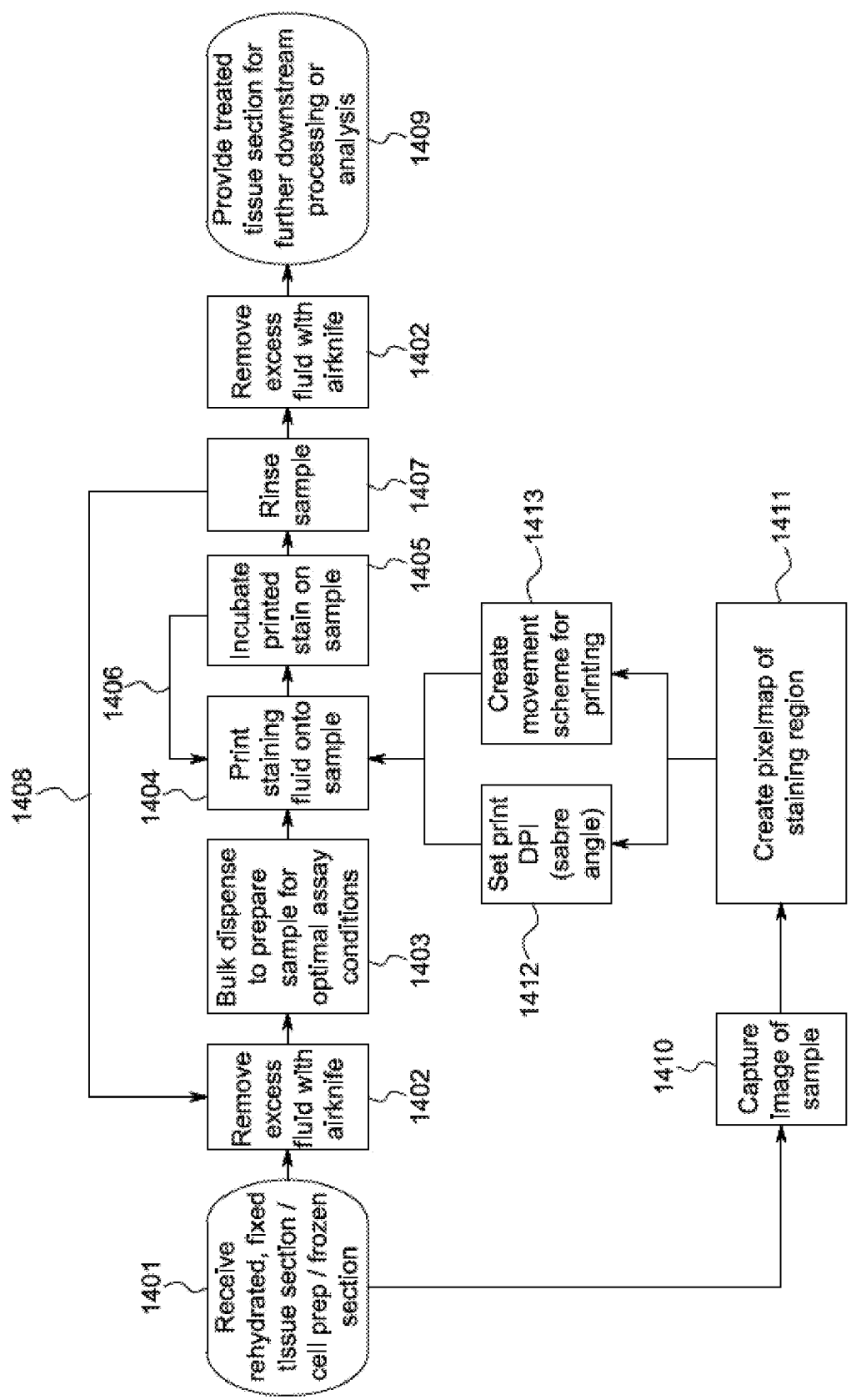
FIG. 3 sets forth a reagent dispensing process according to another embodiment of the present disclosure.
Figure 4A:
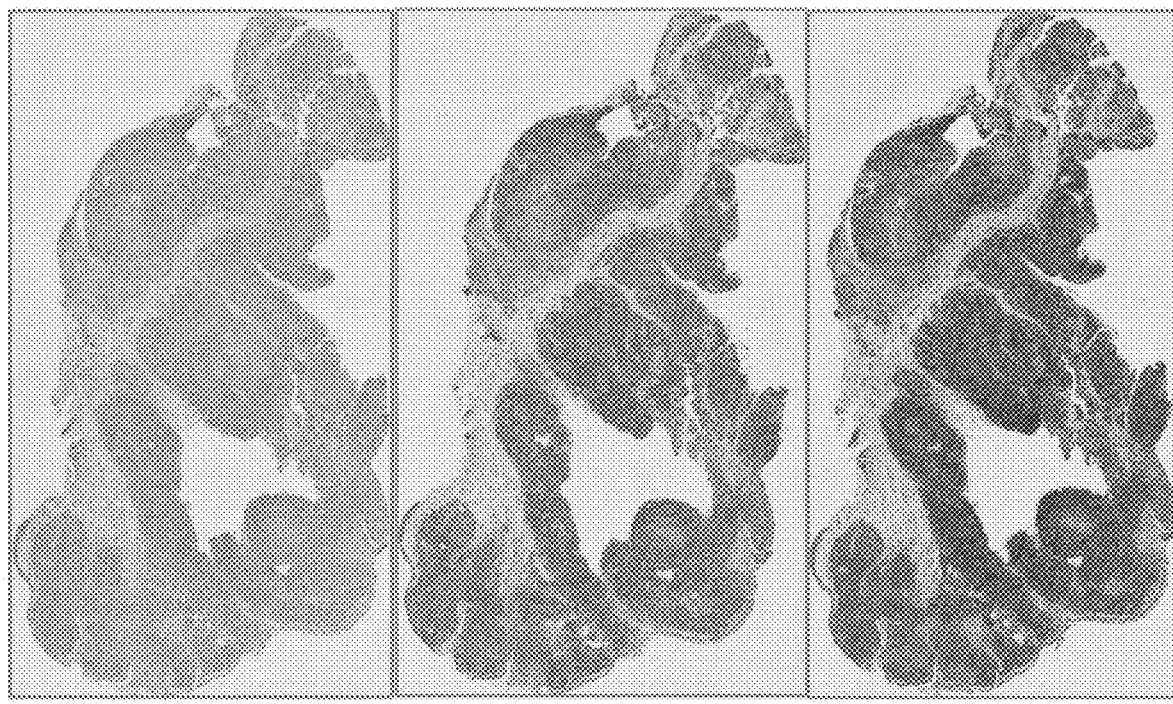
FIGS. 4A through 4E illustrate staining of a tissue sample with hematoxylin, whereby the tissue was stained with a reagent dispensing process according to one embodiment of the present disclosure, and further compares droplet-on-demand staining with conventional staining techniques.

FIG. 3 sets forth another embodiment of an inkjet staining system, which sets forth a staining process utilizing droplet-on-demand technology as developed on a custom inkjet strainer which utilizes a DMC-11610 print head. As will be illustrated further herein, FIG. 4A provides stained tissue samples which were prepared according to the methods outlined herein and as exemplified in FIG. 3. Referring again to FIG. 3, at step 1401, the sample is introduced to the droplet-on-demand staining system (900) and may include a deparaffinized tissue section, a frozen tissue section, or a cell sample. At 1401, an image of the sample is captured (e.g. use the target imaging system 901) including information about the position of the sample with respect to the print heads. This image is, in some embodiments, converted into a stack of pixel maps, with each pixel representing one or more droplets to be ejected from the print head onto respective position on the sample. The stack of pixel maps represents the instructions for each of the print heads to be used in the assay, with one or more layers of the stack partitioned to each of the print heads. At step 1411, instructions are created and/or provided such that the print head may adjust the print dots-per-inch (dpi) (1412) by adjusting the sabre angle at which it prints (see US Patent Publication No. 2009/0314170 for further information regarding sabre angles, the disclosure of which is hereby incorporated by reference herein). In some embodiments, the sabre angle sets the spacing between the nozzles on the DMC-11610 print head. At the same time, the pixel maps are also translated into a series of movements sent to the sample transportation system. The timing of droplet deposition and the relative movement of the sample with respect to the print head during the print operation 1404 are coordinated by a computer system, as illustrated in FIGS. 1A and 1B.

In some embodiments, excess fluid is removed (1402) from the incoming sample. It is believed that this is an integral step leading up to the deposition of stain with droplet deposition technologies since excess fluid may dilute the low volume of stain deposited at 1404 or lead to an inhomogeneous stain deposition. To prepare the sample for staining 1403, a deposition of non-staining fluid is used to adjust the pH and buffer conditions within the tissue sample. In this specific embodiment, this may be performed using a bulk dispense; a print head loaded with the staining preparation fluid; or a combination of two print heads loaded with different buffers that ratiometrically dispense onto the tissue in order to "dial-in" the pH conditions matched to the subsequent staining step(s). As an example of a ratiometric buffer system, Table 2 describes formic acid and acetic acid buffer systems that can be titrated over a range appropriate for preparing the tissue for optimal staining with hematoxylin. Steps 1404, 1405, 1406, and 1407 set forth the process for executing a printed stain, including printing, incubation, a feedback loop for depositing multiple printed layers of the same stain such as to "dial-in" the intensity and specificity of the stain, as noted in FIGS. 1 and 2. After a printed staining step is completed, the sample is rinsed 1407 to remove any unreacted printed reagent and either looped back through the process 1408 to print the next staining step (e.g. a printed eosin step subsequent to a printed hematoxylin step) or released for downstream processing through an air knife (for example) step 1402 to remove excess fluid after which a transformed sample is produced 1409.

The skilled artisan will appreciate that the droplet-on-demand dispensing system may be "tuned" so as to provide different processing parameters depending on the type of reagent dispensed, the type of biological sample, or how the biological sample is prepared. As noted previously herein, some parameters that may be tuned include, but are not limited to, droplet volumes, and droplet velocities. In some embodiments, the droplet-on-demand dispensing system is able to dispense between about 1 pL to about 10 nL of reagent per droplet of the deposition system. In other embodiments, the droplet-on-demand dispensing system is able to dispense between about 1 pL to about 1 nL of reagent per droplet of the deposition system. In yet other embodiments, the droplet-on-demand dispensing system is able to dispense between about 1 pL to about 500 pL of reagent per droplet of the deposition system. In further embodiments, the droplet-on-demand dispensing system is able to dispense between about 1 pL to about 250 pL of reagent per droplet of the deposition system. In yet further embodiments, the droplet-on-demand dispensing system is able to dispense between about 1 pL to about 100 pL of reagent per droplet of the deposition system. In even further embodiments, the droplet-on-demand dispensing system is able to dispense between about 1 pL to about 50 pL of reagent per droplet of the droplet-on-demand dispensing system.

In some embodiments, the reagents are dispensed from the droplet-on-demand dispensing system and/or deposited at a velocity of between about 0.5 m/s to about 20 m/s. In other embodiments, the reagents are dispensed from the device and/or deposited at a velocity of between about 4 m/s to about 10 m/s.

As described further herein, different reagents or compositions comprising reagents may be dispensed from the droplet-on-demand dispensing system. The skilled artisan will appreciate that different reagent compositions or formulations may comprise different properties and, in some embodiments, may be dispensed at different shear rates. By way of example, a primary stain reagent composition (or, for that matter, any small molecule dye) may be dispensed at a shear rate of between about $1 \times 10^5$ s$^{-1}$ and about $1 \times 10^7$ s$^{-1}$. As another example, a large molecule reagent composition may be dispensed at a shear rate less than about $2 \times 10^6$ s$^{-1}$. As a further example, an antibody reagent solution may be dispensed at a shear rate less than about $5 \times 10^5$ s$^{-1}$. Appropriate shear rates may be determined for each composition by those of ordinary skill in the art and the dispensing device may be tuned accordingly.

Applicants submit that the droplet-on-demand dispensing system of the present disclosure allows for precise dispensing of reagents onto a biological sample. Indeed, and as compared to the prior art, the amount or mass of reagent deposited onto the biological sample using the disclosed dispensing device may be varied by "dialing-in" an amount of reagent. The skilled artisan will recognize that an intensity of a stain may thus be varied based on a particular sample and/or assay. Indeed, Applicants have surprisingly discovered that reagent mass may be varied by one of several methods including (i) applying reagent by multiple passes of the dispensing mechanism, such as to provide a cumulative deposition of reagent material (e.g. from 1 to about 25 passes or more); (ii) varying the dots per inch (dpi) of reagent dispensing (e.g. from about 50 dpi to about 1200 dpi); (iii) varying the droplet volume (e.g. from about 1 pl to about 1 nL); and/or (iv) varying the reagent concentration in any reagent composition or formulation.

The present reagent dispensing device is believed to allow for less reagent to be utilized and/or wasted as compared with prior art techniques. Table 1 sets forth various staining processes and comparatively illustrates slide coverage volume per assay step and spatial staining capability between different instruments. Table 1 sets forth reagent volume savings and the ability to stain specific regions of a microscope slide using inkjet or another droplet generation technology in the context of an automated staining tissue staining platform. For assay steps, such as the droplet-on-demand system described herein, the total volumes required to cover an entire sample vary from about ten microliters to about less than a microliter. At the same time, with a single-droplet volume of about ten Pico liters, it is believed that staining specific regions of about ten cells or less is possible. By way of example, and as enumerated in Table 1, as compared with the prior art "dip and dunk" technique which requires about 10 mL to 100 mL of reagent per slide per assay step, the present device only requires, in some embodiments, about 0.001 mL of reagent to be used per slide per assay step, resulting in a significant reduction in the volume of reagent utilized (i.e. several orders of magnitude difference). Moreover, Applicants have discovered that the device according to the present disclosure allows for reaction kinetics to increase when compared with prior art methods, as described further herein.

TABLE 1

Comparison of difference staining processes.

| Staining Process | Example Instrument | Slide Coverage Volume per Assay Step | Spatial Staining Capability |
|---|---|---|---|
| Dip and Dunk | Dako Autostainer LINK 48 | >10 mL per container est. | No |
| Puddle | VENTANA HE 600 system | ~1 mL est. | No |
| Microfluidic | Leica BOND-III | ~100 µL est. | No |
| Droplet Based | Inkjet Stainer (disclosed herein) | <1 to 10 uL | Yes, 10 cell regions est. |

Figure 4B:
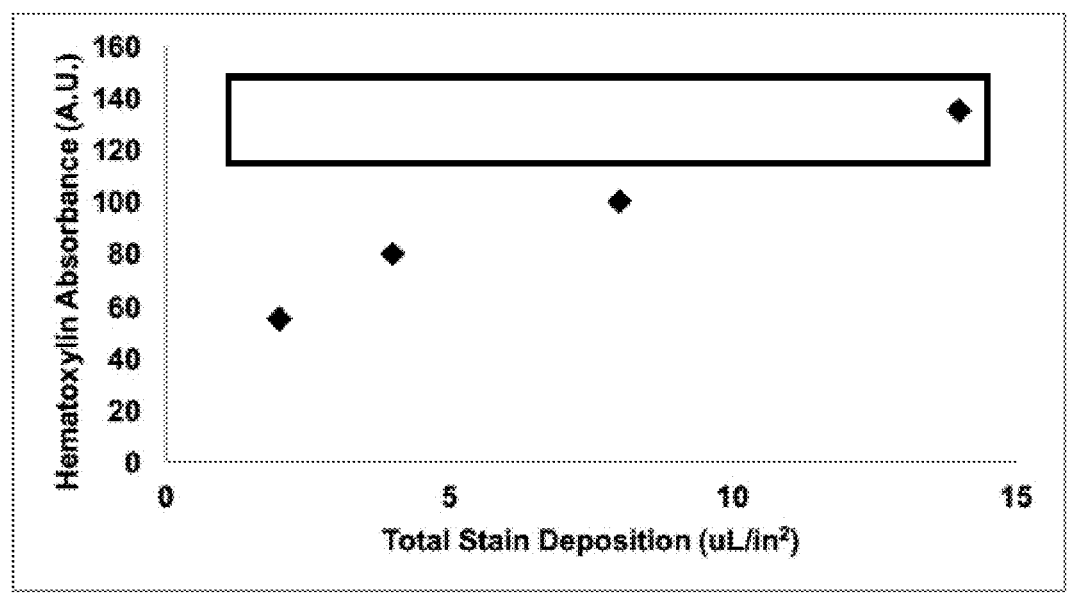
Figure 4C:
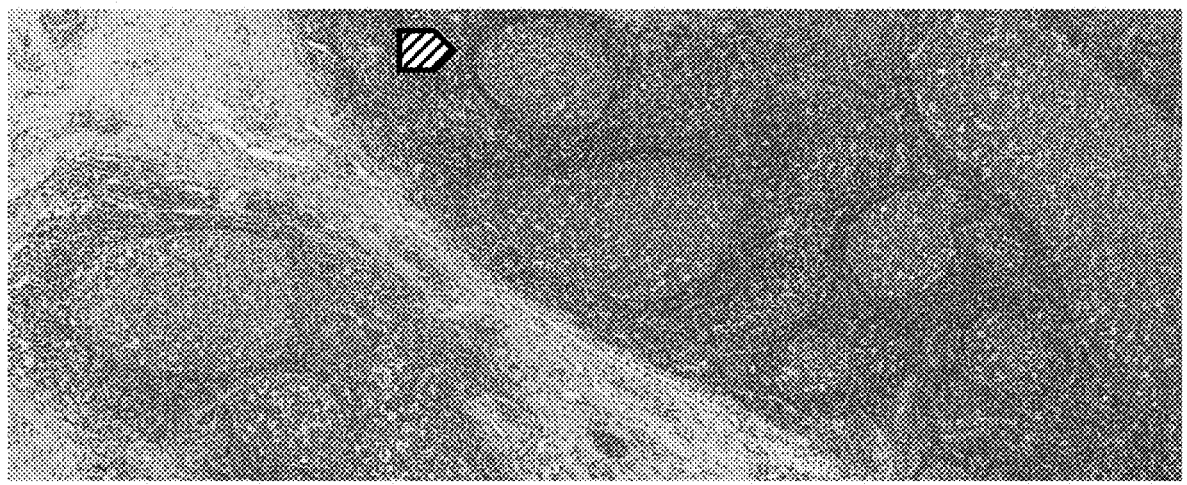
Figure 4D:
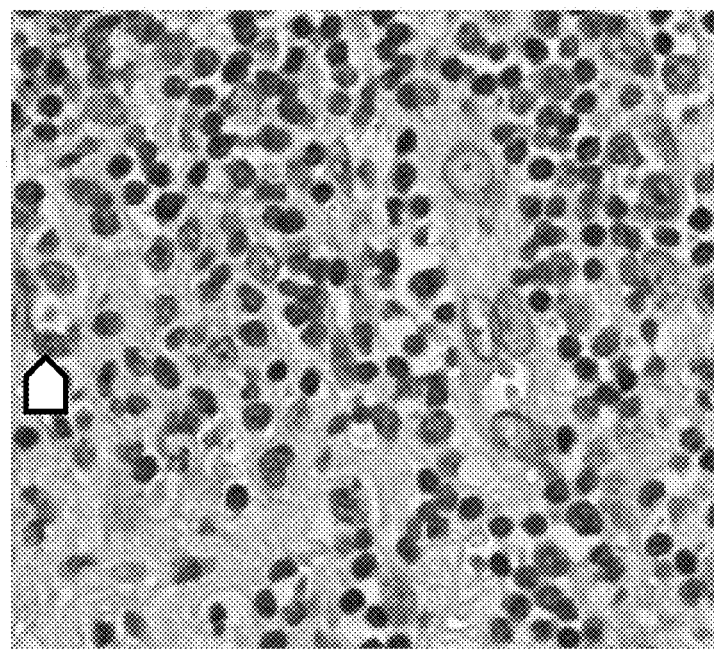
Figure 4E:
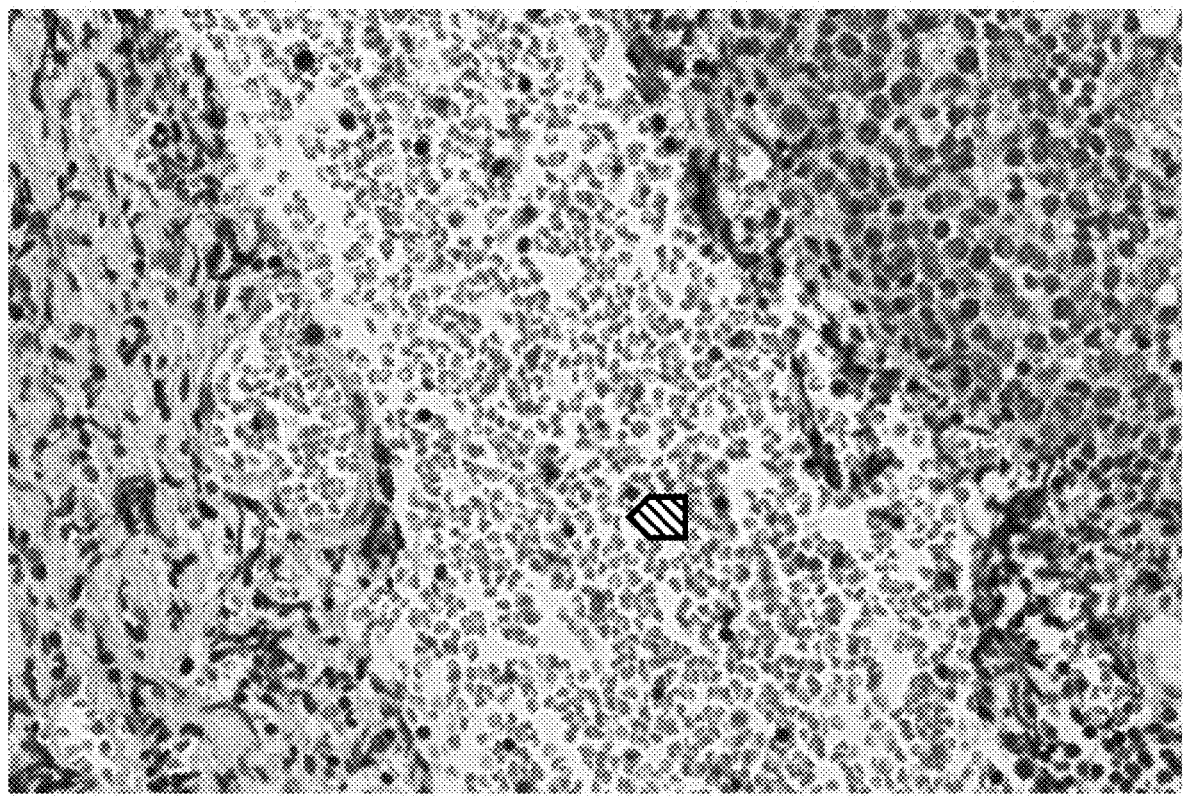

In the context of the primary stains hematoxylin and eosin, as the mass of reagent dispensed increases (as the number of passes increased), the intensity of the stain increases (see, for example, FIGS. 4A to 4E and 5A to 5C). FIGS. 4A to 4E illustrate hematoxylin reagent dispensing onto tonsil tissue fixed on a specimen slide (see Example 6 herein for staining procedures). FIG. 4A qualitatively shows that with an increasing number of passes, and increasing volume of reagent dispensed (4 µL/in$^2$, 8 µL/in$^2$, 14 µL/in$^2$), the staining intensity increases for the inkjet process. FIG. 4B illustrates the absorbance of the hematoxylin primary stain based on the total stain deposition (600 dpi, 3 pL drop size, about 1 µL/in$^2$ per pass of the print head). For comparison with conventional staining apparatuses, absorbance values from control slides are shown in the indicated band of FIG. 4B. About 14 µL/in$^2$ of stain deposition from the reagent dispensing device results in a stain approximately equivalent to that provided with conventional staining apparatus with a two (2) minute incubation time. As an example of staining according to the disclosed methods, FIG. 4C shows crisp staining of lymphoid follicles surrounding germinal centers, a critical macroscopic feature of quality tissue staining, as produced by the inkjet staining process described in this disclosure. In FIG. 4C, the arrow denotes a germinal center with strong staining in the lymphoid follicle rim. FIG. 4D provides a microscopic view of the inkjet stained tonsil tissue and shows distinct nuclear staining, including the ability to see condensed chromatin and nuclear membranes in some nuclei. In FIG. 4D the arrow denotes an example nucleus where condensed nuclear material is visibly darker stained than the surrounding nucleus. FIG. 4E provides a view of a stained tonsil section demonstrating that the disclosed technique provides specific staining; in the field both stained nuclei and unstained red blood cells (denoted by the arrow) are present.

The experimental results illustrated in FIGS. 4A to 4E were obtained using a custom retrofitted EPSON C88+ printer with Non-OEM refillable ink cartridges filled with a modified, commercially available hematoxylin. The print characteristics were as described above. In brief, the experiment consisted of: 1) preparing 4 µm tonsil section from FFPE blocks, 2) preparing the section for staining, 3) creating a print image file to instruct the printer on the reagent to be printed, the x-y coordinates for staining, and the pattern to be printed, 4) loading the tissue section and glass slide onto the print feed mechanism, 5) repeating the printing process to achieve the desired stain intensity, and 6) manually washing off excess stain and coverslipping the slide. Slides were imaged using a VENTANA iScan HT Slide Scanner and intensity values were extracted using ImageJ and MATLAB.

Without wishing to be bound by any particular theory, it is believed that the significance of the results above is two-fold. First, it demonstrates that "dialing-in" staining intensity (mass-limited staining) is enabled by the droplet-on-demand printing process (e.g. inkjet deposition or another small droplet deposition technology). Previously, this has not been a capability of any other tissue staining technology, as all other technologies required a combination of incubation time, temperature, or variable concentration reagents to "dial-in" the intensity of staining Second, the result demonstrates that in this low-volume staining format, tissue dry-out does not result in non-specific staining, as demonstrated by the macroscopic and microscopic features visible in FIGS. 4C, 4D, and 4E.

Figure 5A:
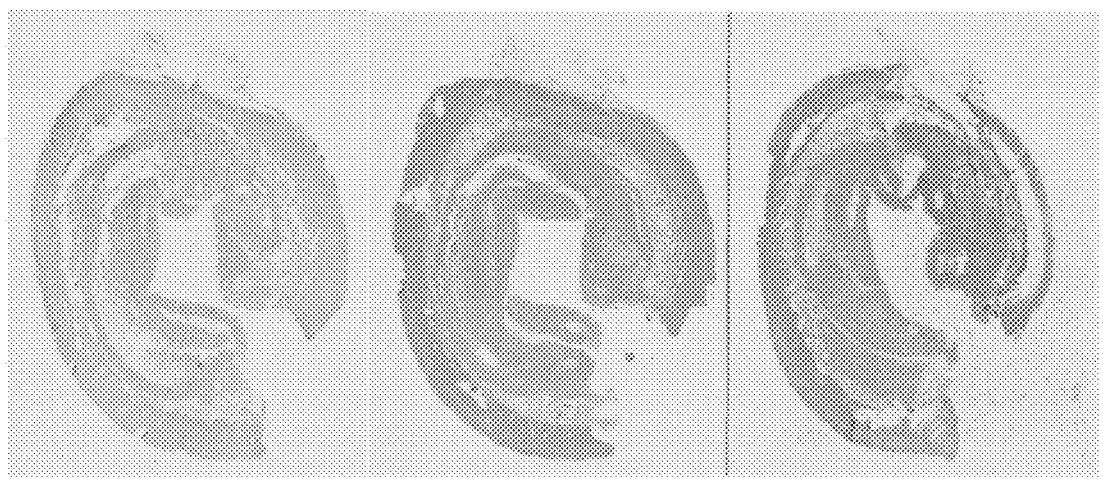
FIGS. 5A through 5C illustrate staining of a tissue sample with eosin, whereby the tissue was stained with a reagent dispensing process according to one embodiment of the present disclosure, and further compares droplet-on-demand staining with conventional staining techniques.
Figure 5B:
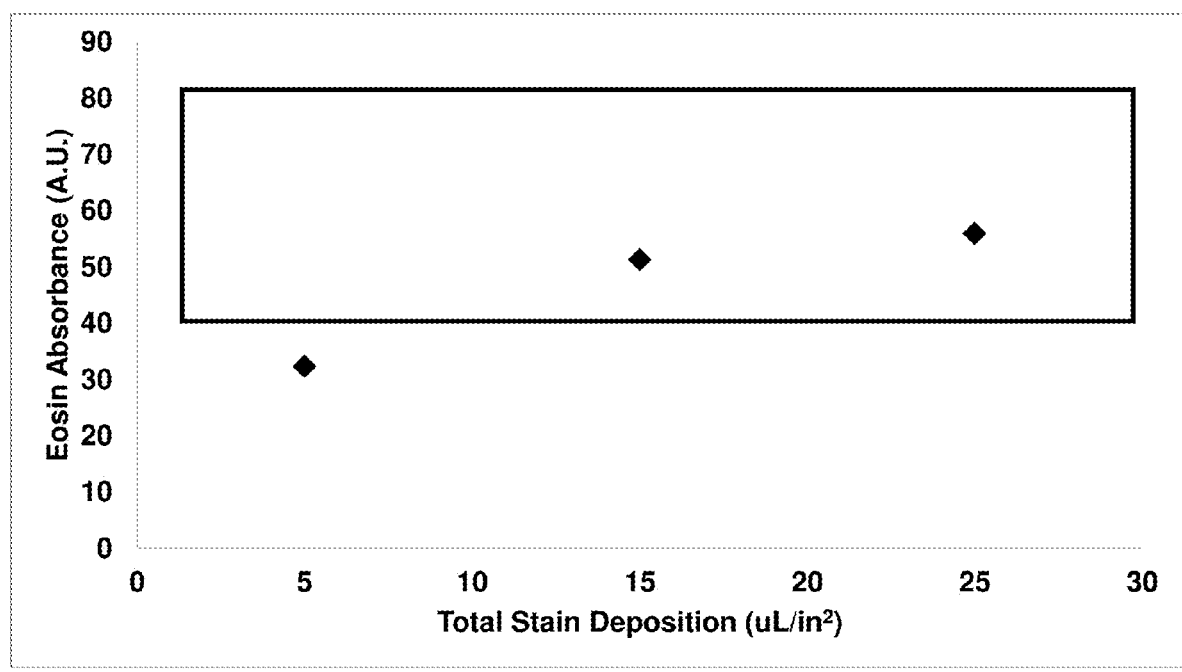
Figure 5C:
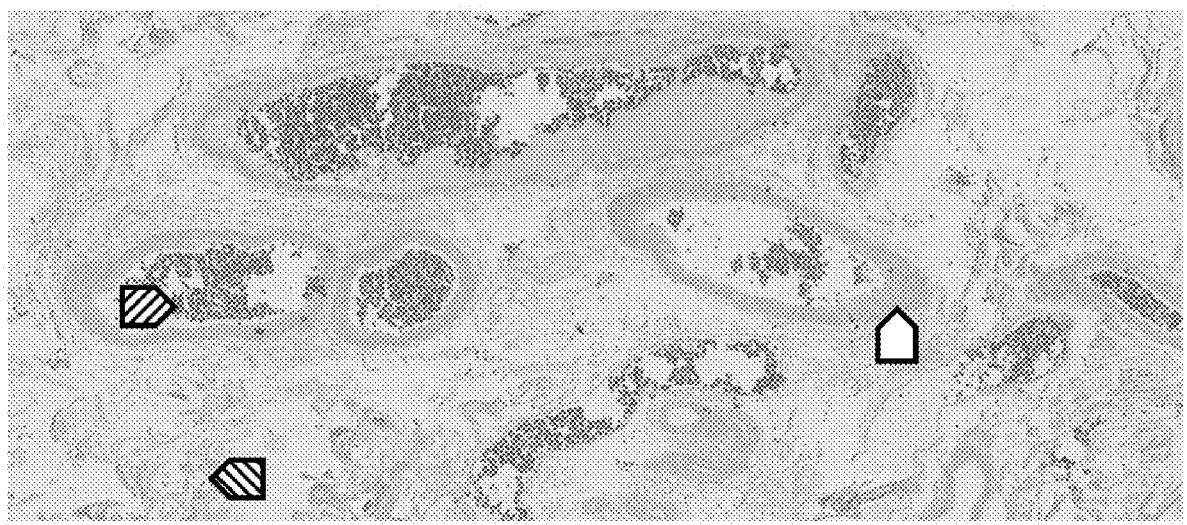

By way of another example, FIGS. 5A to 5C illustrate eosin reagent dispensing onto colon tissue fixed on specimen slides. FIG. 5A illustrates increasing eosin stain intensities with increasing stain deposition (5 µL/in$^2$, 15 µL/in$^2$, 25 µL/in$^2$) utilizing the currently disclosed dispensing device and process. FIG. 5B illustrates the absorbance of the eosin primary stain based on the total stain deposition. For comparison with conventional staining apparatuses, absorbance values from control slides are shown in the shaded band. At about 25 µL/in$^2$ of stain deposition from the reagent dispensing device results in an equivalent stain to a two (2) minute incubation time using a conventional staining apparatus. FIG. 5C compares staining of colon tissue using an inkjet process where three distinct shades of eosin can be clearly observed, and this allows the skilled artisan to differentiate tissue regions (smooth muscles, connective tissue, and red blood cells). In FIG. 5C, the reverse hatched arrow denotes a lightly stained region of connective tissue, the forward hatched arrow denotes an intensely stained region of red blood cells, and the white arrow denotes the moderately stained smooth muscle surrounding a blood vessel. This experimental result was obtained using the procedure described herein with the exception that hematoxylin was substituted for a modified eosin formulation. As in FIGS. 4A to 4E, FIGS. 5A to 5C demonstrate that "dialing-in" stain intensity is enabled by a droplet-on-demand reagent dispensing process and further that a low volume staining environment does not inhibit the required specificity of staining, as evidenced in FIG. 5C.

Figure 6A:
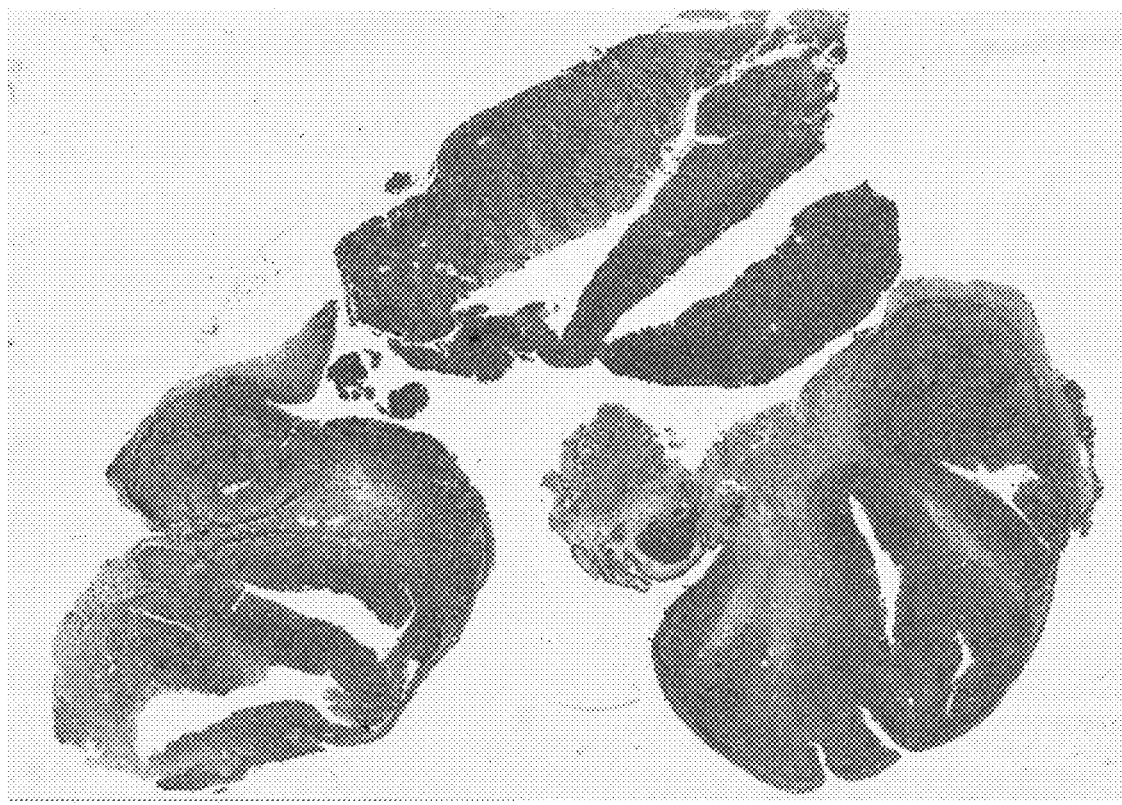
FIGS. 6A and 6B illustrate staining of a tissue sample with both hematoxylin and eosin using a reagent dispensing process according to one embodiment of the present disclosure.
Figure 6B:
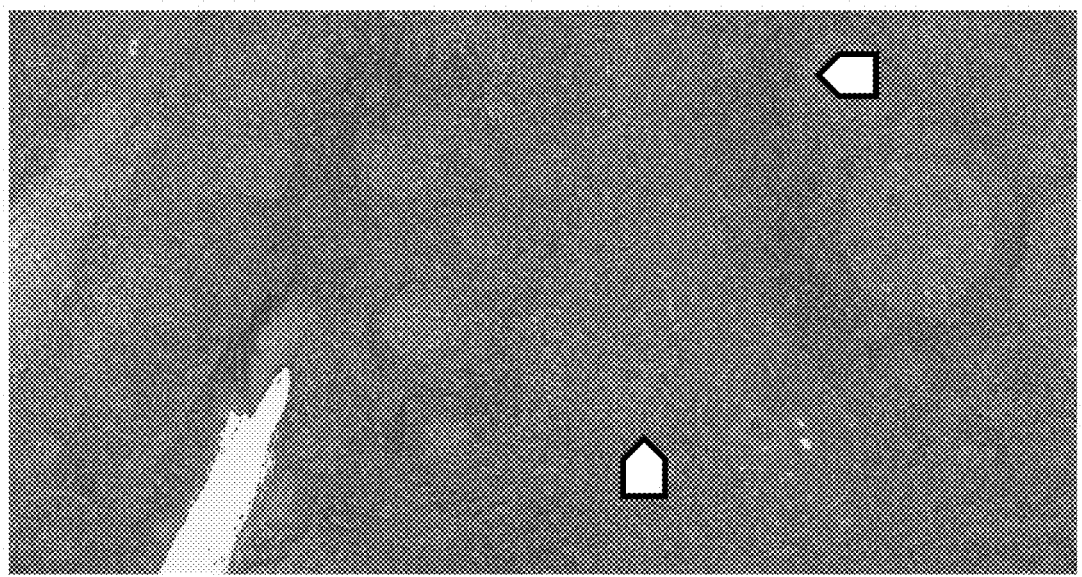

Of course, the skilled artisan will appreciate that stains may be deposited in a multi-step process, e.g. where two primary stains (or any two reagents) are deposited onto a biological sample. FIGS. 6A and 6B provide an illustration of staining with both hematoxylin and eosin primary stains using a droplet-on-demand dispensing device according to the present disclosure, where the total stain volumes deposited were about 8 µL/in² and about 12 µL/in². Applicants have discovered that multiple dispensing staining operations do not interfere and that custom reagents formulated for inkjet technology provide acceptable staining results. FIG. 6A shows the macroscopic staining result, with multiple morphological regions of the tissue stained with the correspondingly different ratios of hematoxylin and eosin, based on the microscopic structure of that feature. FIG. 6B show a magnified view that shows high degrees of nuclear staining on the lymphoid follicles of the germinal centers and a high degree of eosin staining in the connective tissue between the active regions of this tonsil specimen. In FIG. 6B, the left arrow denotes a region of a lymphoid follicle (darker hematoxylin staining) surrounding a germinal center (lighter hematoxylin staining) and the upright arrow denotes a region of squamous epithelium, intensely stained with eosin.

The experimental result of FIGS. 6A and 6B were obtained using the Dimatix DMP-2831 Materials Printer with the Dimatix DMC-11610 print cartridge. The drop size from these 16 nozzle print heads were known to be fixed at about 10 pL and the droplet spacing for the print job was set at about 1270 dpi for the printing of both hematoxylin and eosin. For this stain, custom inkjet formulations for hematoxylin and eosin were developed, as described herein. As noted further herein, these formulations were designed to achieve several objectives including: 1) improved dispensing reliability and consistency through the design of the physical characteristics of the fluids (i.e. setting the appropriate viscosity and surface tension for jet formation and droplet breakoff), 2) improved stability of reagents in the cartridge (e.g. the introduction of Aluminum Chloride to the hematoxylin formulation), and 3) increasing the staining intensity of the formulations to minimize the number of printing passes required (e.g. darker eosin staining is produced with five passes of the "inkjet eosin" as opposed to the 25 passes required for the darkest stain in FIGS. 5A to 5C). The printing processes in this experiment consisted of the following steps: 1) creating a print image file for the position, shape, and size of the tissue section mounted on a glass slide, 2) loading a cartridge and print head for the specific reagent to be printed onto the tissue, 3) setting the sabre angle of the print head to dial in the correct DPI for the staining process, 4) loading the microscope slide and sample onto the movement stage, and 5) executing the print job the desired number of interaction to evolve the proper staining intensity. The application of bluing solution for hematoxylin or a solution to differentiate the eosin was performed manually, offline.

In some embodiments, the reagent deposition device is configured to enable any reagent dispensed to penetrate a thin boundary layer of fluid and replenish staining reagents in communication with the sample. Without wishing to be bound by any particular theory, it is believed that current staining technology relies upon puddles of staining reagents which passively diffuse down a concentration gradient into the tissue sample. In these staining systems, which are believed to lack active mixing of the reagent at the puddle-tissue interface, stain diffusion into tissue is mediated by the buildup of a stain concentration depletion layer at the interface, limiting staining kinetics. The present disclosure is believed to improve upon prior art staining techniques by (i) creating staining films of a thickness approaching that of the depletion layer; and (ii) replenishing stain molecules in the depletion layer, thereby overcoming the limitations of passive stain diffusion.

In some embodiments, the reagent, or composition comprising the reagent, is dispensed through an immiscible fluid with sufficient velocity to drive droplets of reagent through a thin film of tissue-preserving fluid medium. Examples of thin film fluids include, but are not limited to, draksol, linpar, mineral oil, or silicone oil. Generally, favorable attributes include a liquid state at room temperature (e.g. 20-30° C.) low surface tension, and low vapor pressure. The liquid state of the immiscible barrier layer allows for the resupply of aqueous fluids through the barrier. The low surface tension allows for the barrier to be coated onto the sample as a relatively thin film (100 µm in height or less). The low vapor pressure ensures that the barrier layer will be slow to evaporate off of the sample. It is believed that this drives the reagent into a layer in communication below the immiscible fluid. For this embodiment, the kinetic energy (a product of the mass of the droplet and the impact velocity when the droplet hits the film) of the droplet should be greater than the surface tension/energy of the protective layer (plus, provide sufficient additional energy to account for displaced fluid), e.g. great than about $9.52 \times 10^{-10}$ J. In some embodiments, the kinetic energy is about $6.23 \times 10^{-10}$ J. Moreover, the Weber number of the droplet must be less than about 18 to ensure that droplet breakup does not occur on impact. In some embodiments, the droplet must have a higher density than the protective film to ensure that once the surface is broken, the droplet will continue through the protective layer to contact tissue directly.

In other embodiments, the reagent is dispensed into a pre-existing aqueous fluid "puddle" with sufficient velocity that droplets of the reagent are driven into a thin film that will carry stain locally through the puddle to a fluid-tissue stain depletion layer. It is believed that this will facilitate the replenishment of reagent at the interfacial contact point in communication with the sample. In turn, it is believed that this will eliminate the stain depletion boundary layer and improve the staining reaction kinetics which, in some cases, is mediated by the diffusion of staining reagent across the depletion layer. Indeed, for large biomolecules, such as antibodies, binding of the molecule to a target is driven by time and concentration. By continually disrupting the thin film with additional reagent material via dispensing with the presently disclosed device (and inherent mixing), the effective concentration at the tissue surface is enhanced, and believed to provide for faster uptake. For this embodiment, the velocity generally ranges from about 5 m/s to about 15 m/s.

Figure 7:
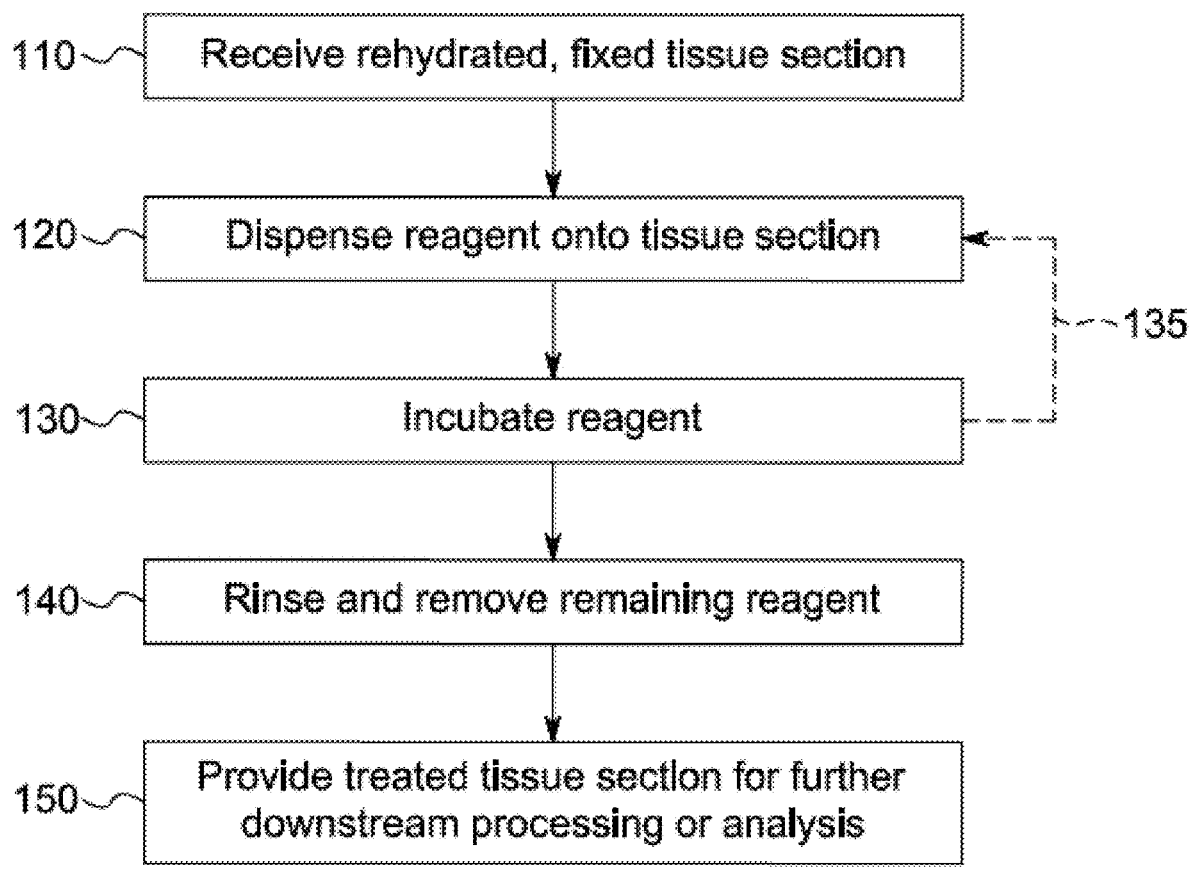
FIG. 7 sets forth a flowchart illustrating one process for staining a tissue sample with a primary stain or an antibody in an IHC process.

With reference to FIG. 7, an incoming slide containing a tissue sample is first received by the device 110. In some embodiments, the tissue sample contains a protective fluid layer in communication with the sample to prevent the sample from drying out. Reagent is then dispensed onto the tissue section 120. Step 120 may be repeated as many times as necessary to build stain intensity. In some embodiments, the reagent is optionally incubated 130. For example, for large biomolecules, binding may be driven by time and concentration. Dispensing with or without incubation may be repeated 135 as necessary. Without wishing to be bound by any particular theory, it is believed that by continually disrupting the thin film with addition dispensed reagent, the effective concentration at the tissue surface is enhanced, resulting in faster uptake. Following dispensing, remaining reagent and/or the protective film is removed at step 140. In some embodiments, removing reagent and/or the protective film is facilitated by dispensing a wash solution to dilute, increase surface tension, and/or to decrease viscosity. The tissue section is then provided at step 150 for further downstream processing or analysis.

Figure 8A:
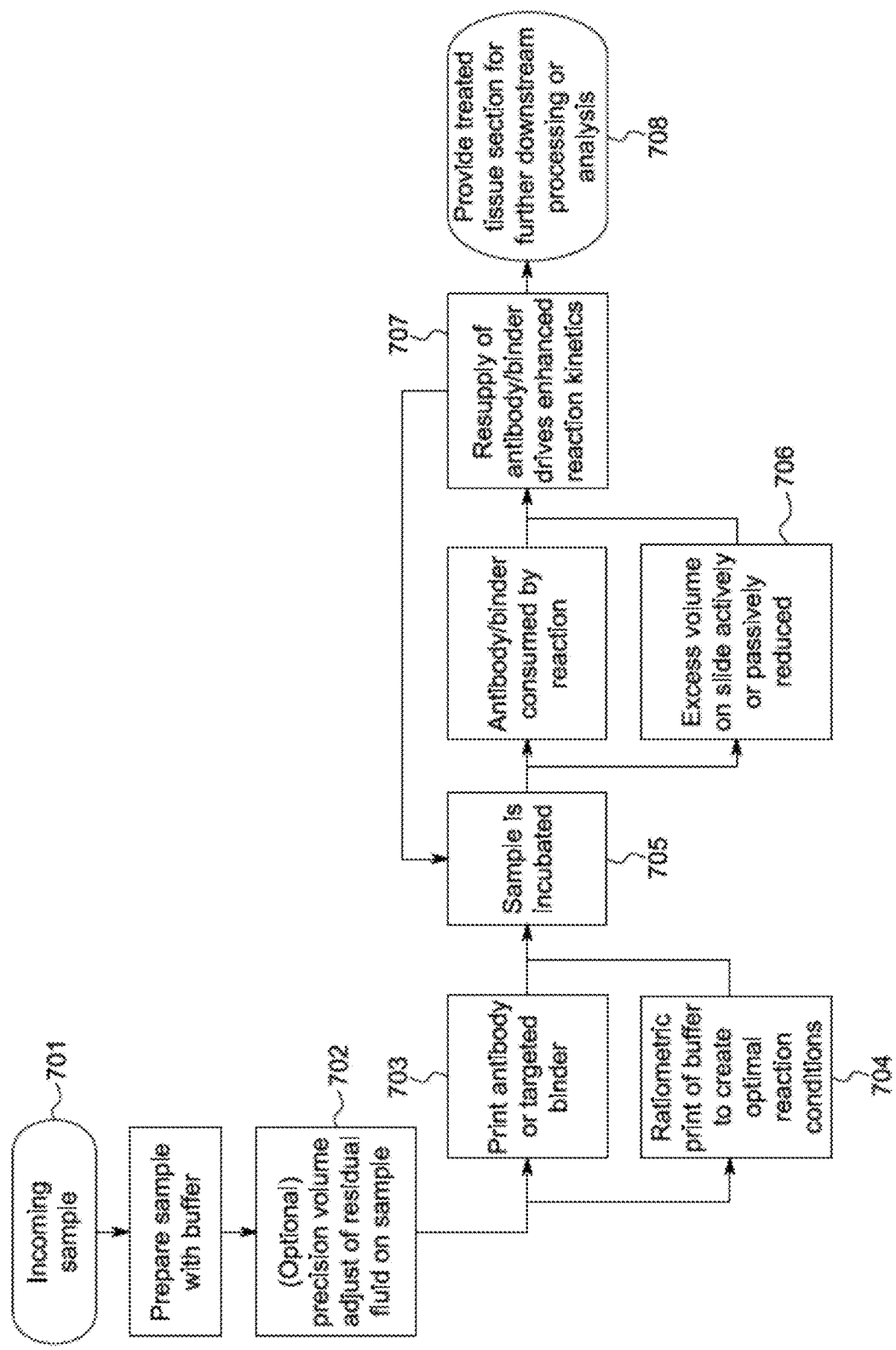
FIG. 8A sets forth a reagent dispensing process according to one embodiment of the present disclosure.

FIG. 8A sets forth a further process map illustrating a process for immunohistochemical staining in an automated fashion using inkjet or other droplet-on-demand technology. At step 701, the incoming sample may include a deparaffinized tissue section, a frozen tissue section, or a cell sample. Step 702 provides a general sample preparation step(s) to bridge from any previous process steps. Generally, this step(s) is designed to ensure that a consistent low volume of residual fluid is present within the sample and that the reaction conditions (e.g. buffer strength, pH) are set appropriately for a subsequent inkjet or droplet-based staining step. The dispense operation at step 702 may be a droplet based process or a bulk fluid dispense onto the sample with a volume from one microliter up to one milliliter. An optional fluid removal portion is designed to precisely reduce the residual volume of fluid remaining on the sample, to a final volume in the range of about 100 nL to about 100 µL. Step 703 sets forth the introduction of a targeted protein binder to the tissue via an inkjet or droplet dispense technology, which encompasses individual droplet size from about 1 pL to about 100 nL, print patterns as small as a single droplet up to the size of a standard microscope slide, and print densities from about 100 dpi to about 1300 dpi.

Step 704 sets forth the optional practice of simultaneously co-dispensing another reagent with the reagent of interest for the particular assay step. For small droplets, it is believed that this facilitates near-instant, on-slide mixing of reagents and imparts the unique ability to mix reagents in-situ to trigger reactions; ratiometrically dilute the concentration of biomolecules, dyes, or substrates; or homogenize the staining field across a sample. Step 705 sets forth the period over which specific binding interactions occur between the dispensed reagent and the target sample. Step 706 sets forth the effects occurring to the deposited print droplets onto the tissue whereby the small amount of active binder is consumed via reaction with the tissue while the excess fluid is either actively or passively removed from the sample. Since it is believed that these small volumes are thinner than the expected diffusion depletion layer observed in puddle staining technology, these reactions are believed to proceed quickly and as a result may be replenished with additional active binders to continue to rapidly drive the reaction toward the desired endpoint or equilibrium.

Step 707 sets forth the means by which additional active binders are (biomolecules or dyes) are resupplied to the sample in order to continue driving an efficient reaction. In this case the necessary print density for re-supply may be much smaller than the original print application. In some embodiments, a droplet density of between about 50 to about 100 dpi may be sufficient to drive the reaction, while in other embodiments a complete re-print of the original print density may be required. Finally, in step 708 the sample has completed this assay block and is ready to move on to the next assay block, which may be a repeat of this process but with different reagents and reaction conditions or may be a different process, such as automated coverslipping or imaging as part of an integrated digital pathology workflow.

Figure 8B:
FIG. 8B illustrates a tissue sample staining using a reagent dispensing process according to one embodiment of the present disclosure.

FIG. 8B provides an example result from staining according to the process of FIG. 8A. This example illustrates the result of the deposition of an anti-CD20 primary antibody onto a FFPE section of tonsil, sectioned at 4 µm. The inkjet reagent used in this particular example is described further herein. Generally, the process is applicable for primary antibodies, secondary antibodies, linkers for enzyme mediated detection, enzymes for driving detection reactions, or substrate to the specifically linked enzyme. The process described here is a non-obvious extension of the theory behind "Cyclic draining-replenishing" technology, as described by Li, et al. (Small, 2016, 12, No. 8, 1035-1043). In fact, the process described herein is believed to overcome some limitations of the process described by Li in the sense that the resupply of reagent is directed with a non-zero velocity into the tissue via an inkjet print head (approximately 8 m/s in this example). Further, in the work by Li, the focus was on a circular mixing process while in the present disclosure either an active (e.g. air flow) or passive (e.g. evaporation) process is used to drain the excess fluid while the dye or biological is resupplied via additional print passes with the inkjet head (see step 707 of FIG. 8A). This in turn is believed to drive the reaction speed from a diffusion-mediated process (slow, characteristic of puddle-based staining technologies) to a binding kinetics mediated process (fast, unique to droplet deposition and film-based staining techniques where the depletion layer can be actively resupplies with biomolecules or dye).

Figure 9A:
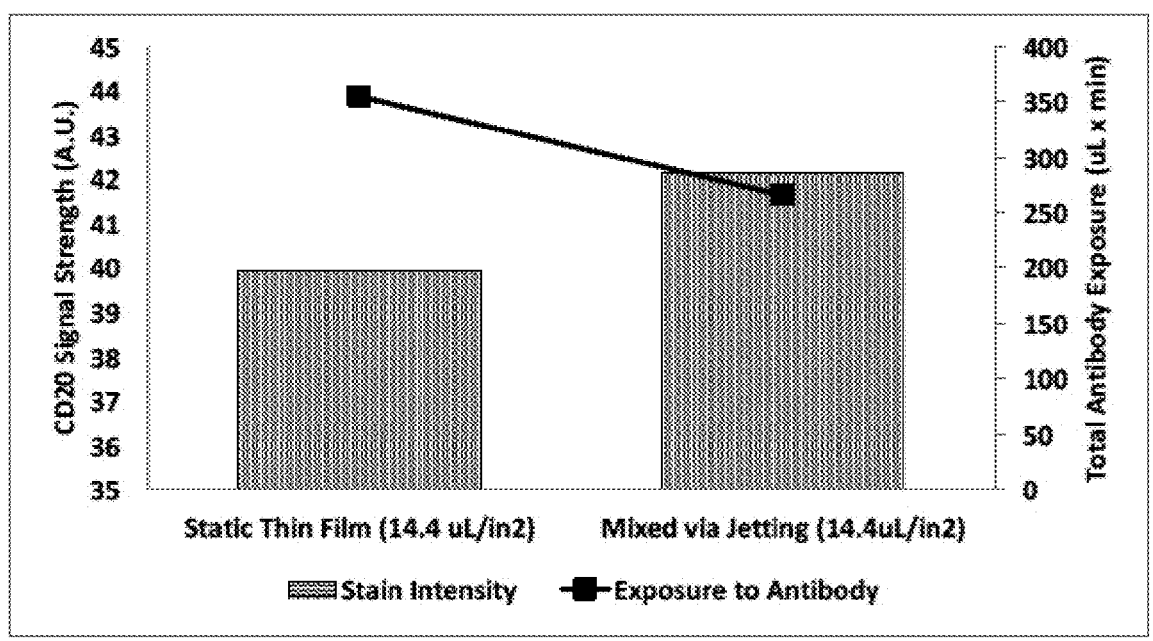
FIGS. 9A, 9B, and 9C illustrate staining achieved through deposition of primary antibodies using a reagent dispensing process according to one embodiment of the present disclosure.
Figure 9B:
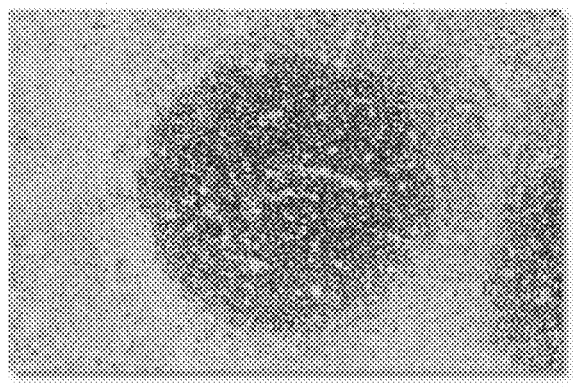
Figure 9C:
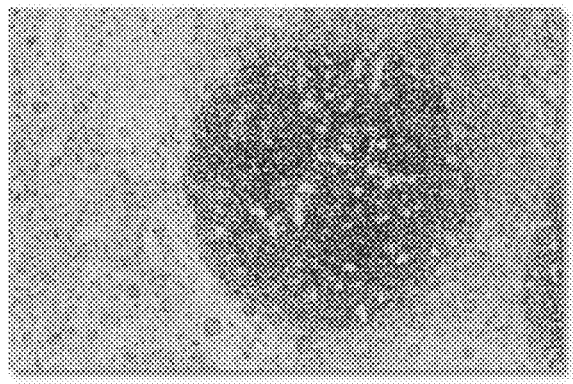

FIGS. 9A, 9B, and 9C further illustrate the staining achieved through the deposition of primary antibodies using the droplet-on-demand system and methods disclosed herein. In general, FIGS. 9A, 9B, and 9C set forth examples of primary antibodies deposited using a droplet-on-demand process, using anti CD-20 antibodies on tonsil tissue. FIG. 9A compares staining intensity for a static thin film puddle versus a mixed thin film puddle. In this case, despite a lower total antibody exposure (µL× time), the thin film mixed via jetting of fluid into the film resulted in a higher stain intensity. Details of the mechanism driving these differential results are illustrated in FIG. 8A. FIGS. 9B and 9C show regions of tonsil tissue stained according to the processes stained herein, where for FIG. 9B the parameters are as follows: 14.4 µL/in$^2$ (1200 dpi, 10 pL drop, single print head pass), static film, 16-minute incubation time. For FIG. 9C the parameters are as follows: 3.6 µL/in$^2$ (600 dpi, 10 pL drop size, single print head pass), four (4) minute incubation time, mixing via the addition of 400 nL/in$^2$ (200 dpi, 10 pL drop size, single print head pass) of antibody to the thin film then another four (4) minute incubation, followed by two (2) additional mixing steps.

Figure 10A:
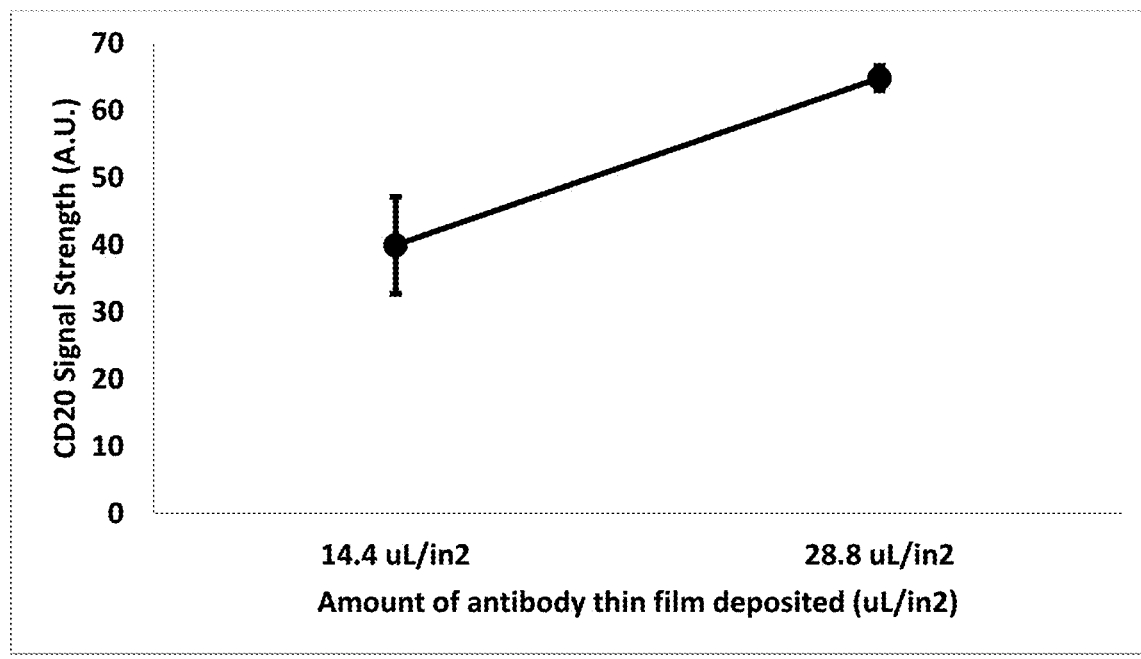
FIGS. 10A through 10C illustrate additional examples of the deposition of primary antibodies using a reagent dispensing process according to one embodiment of the present disclosure.
Figure 10B:
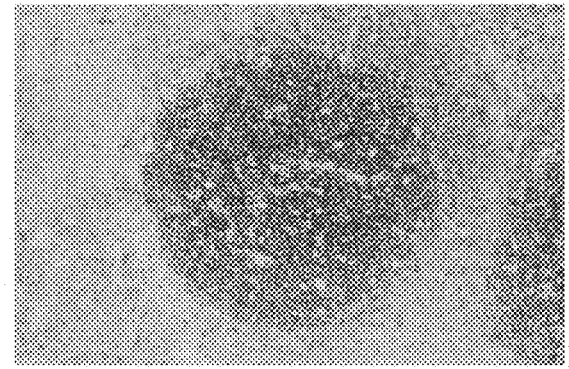
Figure 10C:
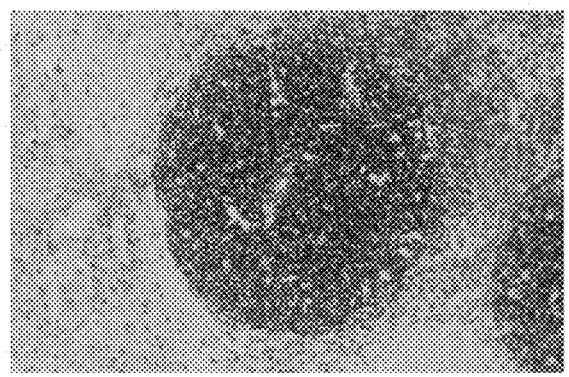

FIGS. 10A through 10C provide additional examples of the deposition of primary antibodies deposited using a droplet-on-demand reagent deposition process according to the present disclosure (anti-CD20, tonsil tissue). FIGS. 10A to 10C further affirm that inkjet or droplet deposition technologies provide sufficiently small fluid volumes such that binding kinetics are driven by the mass of reagent deposited onto the target. FIG. 10A compares staining intensity for thin film puddles of two different volumes to demonstrate that antibody binding for the inkjet thin film process is mediated by the amount of antibody deposited (i.e. CD20 signal strength increases as a function of the amount of primary antibody deposited on the tissue). FIGS. 10B and 10C are regions of tonsil stained with the respective processes from FIG. 10A. Briefly, for FIG. 10B, 14.4 µL/in$^2$ (1200 dpi, 10 pL drop, single print head pass) of reagent was patterned as a static film onto the tissue section, and allowed to incubate at room temperature for 16 minutes. For FIG. 10C, 28.8 µL/in$^2$ (1200 dpi, 10 pL drop, two (2) print head passes) of reagent was patterned as a static film onto the tissue section, and allowed to incubate at room temperature for 16 minutes. Antibody formulations used to prepare FIGS. 10A through 10C are described further herein.

In another aspect of the present disclosure, Applicants have found that the dispensing device of the present disclosure allows for x-y spatial control of reagent deposition, such that tissue regions of interest may be identified and stain selectively applied to those regions of a biological sample. In some embodiments, the dispensing device described herein is combined with an imaging system such that particular regions or cells within a sample may be treated with a reagent. In another aspect of the present disclosure is a method of applying at least one reagent to a specific region of a tissue specimen comprising the steps of (a) imaging a tissue sample; (b) choosing a specific region of the tissue for application of the reagent; and (c) depositing the reagent to the specific region of the tissue with a piezoelectric deposition system. In some embodiments, between about 360 nL/in$^2$ (600 dpi, 1 pL/drop) to about 14.4 µL/in$^2$ (1200 dpi, 10 pL/drop) of reagent is applied to the specific region of the tissue per pass of the deposition system.

Figure 11:
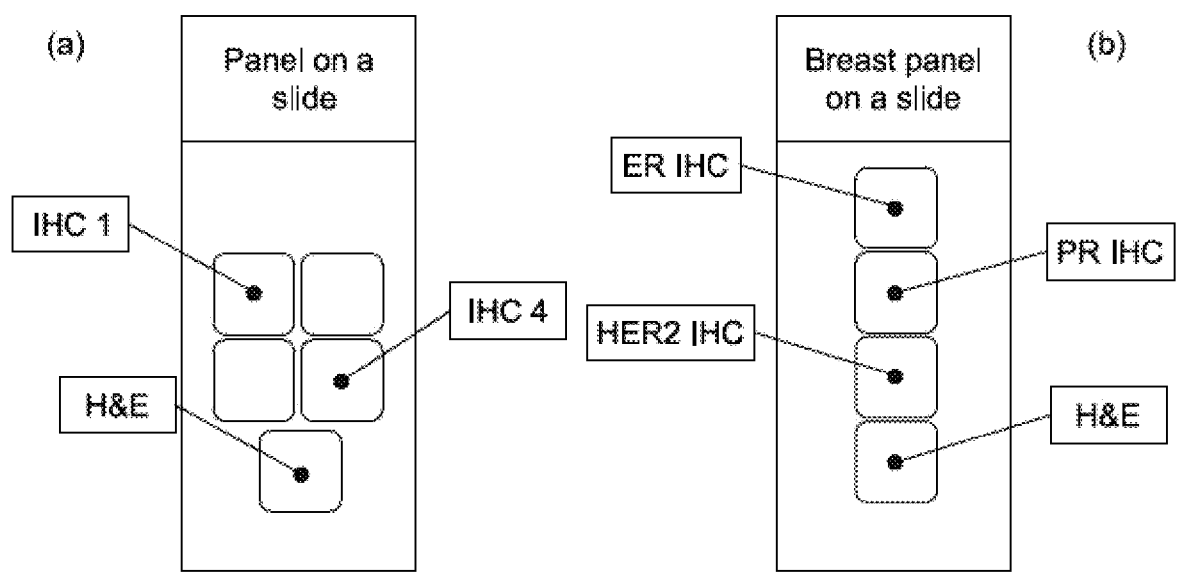
FIG. 11 illustrates staining of different tissue regions with different reagents.

For example, FIG. 11 illustrates a "tissue panel on a slide" embodiment which is enabled specifically by the spatial deposition/multiplexing made possible using the disclosed inkjet staining process. With reference to FIG. 11, antibodies for the IHC stains (labeled IHC1 and IHC4) are incubated on adjacent tissue sections simultaneously. At the same time, a primary stain (labeled H&E) is prepared on another region of the slides. After incubation with primary antibodies, the same or different detection chemistry may be used on the IHC tissue sections since the primary antibodies are spatially separated onto different tissue sections on the slide. It is believed that this would facilitate a quicker assay turnaround time as well as the convenience of a complete diagnostic panel on a single slide. In some embodiments, again with reference to FIG. 11, a three (3) IHC marker breast panel may be run on a single slide, facilitating a pathologist workflow from the morphological staining with a primary stain through each of three diagnostic IHC markers for phenotyping breast cancer (e.g. HER2/neu, Estrogen Receptor, Progesterone Receptor).

Reagent Compositions

Overview

The skilled artisan will appreciate that any type of reagent or reagent composition may be dispensed using the reagent deposition device and process described herein. For example, in some embodiments, the reagent dispensed from the dispensing device is a primary stain, such as hematoxylin or eosin. In other embodiments, the reagent dispensed from the device is an antibody useful in histochemistry (e.g. primary and secondary antibodies), a composition comprising an antibody or antibody conjugate (e.g. enzyme conjugated antibodies, or an antibody conjugated to a fluorophore, hapten, or other label), and/or detection reagents for detecting an antibody or antibody-target complex (e.g. a composition comprising chromogenic substrates, secondary antibodies specific for a label conjugated to a primary antibody, etc.).

In some embodiments, the reagents or compositions comprising reagents are modified as compared with off-the-shelf reagents or compositions comprising those reagents so as to better facilitate delivery and dispensing through an inkjet deposition apparatus or piezoelectric deposition apparatus. For example, the reagents or compositions comprising the reagents may be altered to have a certain density, pH, viscosity, or rheology. In some embodiments, any reagent composition may comprise one or more of buffers, rheology modifiers, surfactants, carrier proteins, stabilizers, viscosity modifiers, humectants, preservatives, and other additives. The skilled artisan will be able to select appropriate components in appropriate amounts to provide a reagent composition having desirable properties so as to effectuate dispensing with inkjet technology.

In some embodiments, the reagent compositions of the present disclosure have a rheology, i.e. a "flow" of the solution, to facilitate a single droplet of reagent under one unit of excitation of piezo-membrane. Indeed, the reagent solutions of the present disclosure have been developed such that they (i) allow for proper staining, (ii) are able to form stable thin films; and (iii) are able to be dispersed via piezoelectric deposition. In some embodiments, the reagent compositions have a density that is greater than about 1 g/mL. In other embodiments, the reagent compositions have a density that is between about 0.75 g/mL and about 1.5 g/mL.

In some embodiments, the viscosity of the reagent composition ranges from about 1 cp to about 40 cp. In other embodiments, the viscosity of the reagent composition ranges from about 4 cp to about 15 cp. In yet other embodiments, the viscosity of the reagent composition ranges from about 6 cp to about 10 cp. In some embodiments, the surface tension of the reagent composition ranges from about 20 dyne/cm to about 70 dyne/cm. In other embodiments, the surface tension of the reagent composition ranges from about 20 dyne/cm to about 45 dyne/cm. In yet other embodiments, the surface tension of the reagent composition ranges from about 20 dyne/cm to about 35 dyne/cm In general, the viscosity modifier for use in any of the reagent compositions is selected from glycols such as ethylene glycols, diethylene glycol, polyethylene glycols, propylene glycols, dipropylene glycols, glycol ethers, glycol ether acetates; saccharides and polysaccharides such as guar gum, xanthan gum; celluloses and modified celluloses such as hydroxy methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, the compositions of the present disclosure may also comprise one or more low-volatile water soluble humectants. Representative examples of humectants include: (1) triols, such as; glycerol, 1,2,6-hexanetriol, 2-ethyl-2-hydroxymethyl-propane diol, trimethylolpropane, alkoxlated triols, alkoxylated pentaerythritols, saccharides, and sugar alcohols; and (2) diols, such as ethylene glycol, diethylene glycol, triethylene glycol, propylene glycol, polyalkylene glycols having four or more alkylene oxide groups, 1,3-propane dial, 1,2-butane diol, 1,3-butane diol, 1,4-butane diol, 1,2-pentane diol, 1,5-pentanediol, 1,2-hexanediol, 1,6-hexane diol, 2-methyl-2,4-pentanediol, 1,2-heptane diol, 1,7-hexane diol, 2-ethyl-1,3-hexane diol, 1,2-octane diol, 2,2,4-trimethyl-1,3-pentane diol, 1,8-octane diol; and thioglycol or a mixture thereof. Desirable humectants are polyhydric alcohols.

In some embodiments, the reagent compositions comprise one or more stabilizers. In general, the stabilizer may be selected from sodium iodate, aluminum chloride hexahydrate, aluminum sulfate hexadecahydrate, and protein stabilizers (e.g. trehalose, glycerol, Globulins, BSA, etc.). It is believed that the inclusion of one or more stabilizers may prevent the precipitation of reagent molecules. For example, hematoxylin, which is known in the art to precipitate out of solution, may be formulated with one or more stabilizers to mitigate or prevent precipitation out of solution, and thus avoid the clogging of reagent lines or print/inkjet dispensing heads.

In some embodiments, the surface tension modifier is a surfactant. The surfactant may be one of an anionic surfactant, a cationic surfactant, a non-ionic surfactant, or mixtures thereof. In some embodiments, an appropriate surfactant is selected such that (i) when combined with the other reagent components, it allows for the desired surface tension to be achieved; (ii) does not denature proteins or other reagent components; and/or (iii) it provides a low foam height.

Anionic surfactants are generally based upon sulfates, sulfonates, phosphates, or carboxylates and contain a water-soluble cation. A representative formula of a sulfonate is R—SO3M where R is a hydrocarbon group of from about 5 to 22 carbon atoms which may be linked through an alkoxy or oxyalkoxy to the sulfonate functionality and M is a water-soluble cation such as an alkali metal. Anionic surfactants include alkyl ether sulfates, alkyl sulfates and sulfonates, alkyl carboxylates, alkyl phenyl ether sulfates, sodium salts of alkyl poly(oxyethylene) sulfonates, sodium salts of alkyl benzyl sulfonate, such as sodium salts of dodecylbenzyl sulfonate and sodium lauryl ether sulfate. Anionic surfactants also include anionic phosphate esters.

In some embodiments, the surfactants include, but are not limited to polyoxyethylene alkyl ether, wherein the alkyl is $(CH_2)_M$ and the oxyethylene is $(C_2H_4O)_N$, wherein M is an integer from 5 to 16, from 8 to 14, or from 10 to 12 and N is an integer from 10 to 40, from 15 to 30, or from 20 to 28. In one embodiment, the surfactant is polyoxyethylene lauryl ether having a formula $(C_2H_4O)_{23}C_{12}H_{25}OH$. In another embodiment, the surfactant is a polyoxyethylene (20) sorbitan monoalkylate, the monoalkylate comprising between 8 and 14 carbons. In another embodiment, the surfactant is a linear secondary alcohol polyoxyethylene having a formula $C_{12-14}H_{25-29}O(CH_2CH_2O)_x$, wherein x equals an integer between 2 and 12. In yet another embodiment, the surfactant is a polyoxyethylene octyl phenyl ether. Exemplary surfactants are sold under the names: Brij® 35, TWEEN®, Tergitol™, Triton™, Ecosurf™, Dowfax™, polysorbate 80™, BigCHAP, Deoxy BigCHAP, IGEPAL®, Saponin, Thesit®, Nonidet®, Pluronic F-68, digitonin, deoxycholate, and the like. Particular disclosed working embodiments concern using surfactants selected from Brij® 35, TWEEN®, Tergitol™, Triton™.

Cationic surfactants useful in compositions of the present disclosure contain amino or quaternary ammonium moieties. Cationic surfactants among those useful herein are disclosed in the following documents: M.C. Publishing Co., McCutcheon's, Detergents & Emulsifiers, (North American edition 1979); Schwartz, et al.; Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

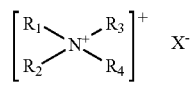

wherein R1-R4 are independently an aliphatic group of from about 1 to about 22 carbon atoms or an aromatic, alkoxy, polyoxyalkylene, alkylamido, hydroxyalkyl, aryl or alkylaryl group having from about 1 to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated. Especially preferred are mono-long chain (e.g., mono $C_{12}$ to $C_{22}$, preferably $C_{12}$ to $C_{18}$, more preferably $C_{16}$, aliphatic, preferably alkyl), di-short chain (e.g., $C_1$ to $C_3$ alkyl, preferably $C_1$ to $C_2$ alkyl) quaternary ammonium salts.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (with 5 moles of ethylene oxide) stearylamine, dihydroxy ethyl stearylamine, and arachidylbehenylamine. Suitable amine salts include the halogen, acetate, phosphate, nitrate, citrate, lactate, and alkyl sulfate salts. Such salts include stearylamine hydrochloride, soyamine chloride, stearylamine formate, N-tallowpropane diamine dichloride, stearamidopropyl dimethylamine citrate, cetyl trimethyl ammonium chloride and dicetyl diammonium chloride. Preferred for use in the compositions herein are cetyl trimethyl ammonium chloride, stearyl trimethyl ammonium chloride, tetradecyltrimethly ammonium chloride, dicetyldimethyl ammonium chloride, dicocodimethyl ammonium chloride and mixtures thereof. More preferred is cetyl trimethyl ammonium chloride.

The compositions of the disclosure may also include various non-ionic surfactants. Among the suitable nonionic surfactants are condensation products of $C_8$-$C_{30}$ alcohols with sugar or starch polymers. These compounds can be represented by the formula $(S)_n$—O—R, wherein S is a sugar moiety such as glucose, fructose, mannose, and galactose; n is an integer of from about 1 to about 1000, and R is $C_8$-$C_{30}$ alkyl. Examples of suitable $C_8$-$C_{30}$ alcohols from which the R group may be derived include decyl alcohol, cetyl alcohol, stearyl alcohol, lauryl alcohol, myristyl alcohol, oleyl alcohol, and the like. Specific examples of these surfactants include decyl polyglucoside and lauryl polyglucoside.

Other suitable nonionic surfactants include the condensation products of alkylene oxides with fatty acids (i.e., alkylene oxide esters of fatty acids). These materials have the general formula $RCO(X)_nOH$, wherein R is a $C_{10}$-$C_{30}$ alkyl, X is —OCH$_2$CH$_2$— (derived from ethylene oxide) or —OCH$_2$CHCH$_3$— (derived from propylene oxide), and n is an integer from about 1 to about 200.

Yet other suitable nonionic surfactants are the condensation products of alkylene oxides with fatty acids (i.e., alkylene oxide diesters of fatty acids) having the formula $RCO(X)_nOOCR$, wherein R is a $C_{10}$-$C_{30}$ alkyl, X is —OCH$_2$CH$_2$— (derived from ethylene oxide) or —OCH$_2$CHCH$_3$— (derived from propylene oxide), and n is an integer from about 1 to about 200. Yet other nonionic surfactants are the condensation products of alkylene oxides with fatty alcohols (i.e., alkylene oxide ethers of fatty alcohols) having the general formula R(X)$_n$OR', wherein R is C$_{10}$-C$_{30}$ alkyl, n is an integer from about 1 to about 200, and R' is H or a C$_{10}$-C$_{30}$ alkyl.

Still other nonionic surfactants are the compounds having the formula RCO(X)$_n$OR' wherein R and R' are C$_{10}$-C$_{30}$ alkyl, X is —OCH$_2$CH$_2$— (derived from ethylene oxide) or —OCH$_2$CHCH$_3$— (derived from propylene oxide), and n is an integer from about 1 to about 200. Examples of alkylene oxide-derived nonionic surfactants include ceteth-1, ceteth-2, ceteth-6, ceteth-10, ceteth-12, ceteraeth-2, ceteareth6, ceteareth-10, ceteareth-12, steareth-1, steareth-2, stearteth-6, steareth-10, steareth-12, PEG-2 stearate, PEG4 stearate, PEG6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof. Still other useful nonionic surfactants include polyhydroxy fatty acid amides disclosed, for example, in U.S. Pat. Nos. 2,965,576, 2,703, 798, and 1,985,424, which are incorporated herein by reference.

Exemplary surfactants include Tomadol 1200 (Air Products), Tomadol 900 (Air Products), Tomadol 91-8 (Air Products), Tomadol 1-9 (Air Products), Tergitol 15-S-9 (Sigma), Tergitol 15-S-12 (Sigma), Masurf NRW-N (Pilot Chemical), Bio-Soft N91-6 (Stepan), and Brij-35 (Polyethylene glycol dodecyl ether) (Sigma).

Figure 12A:
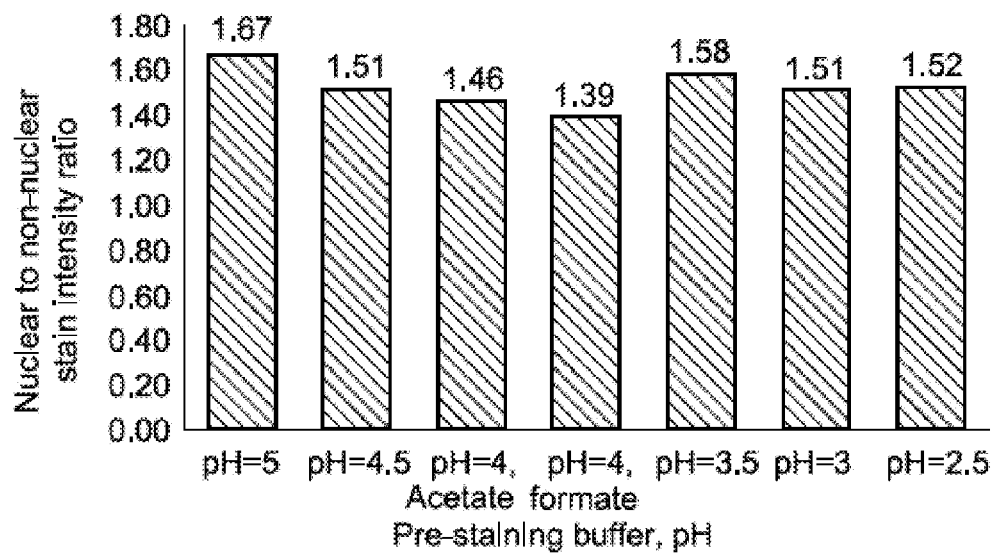
FIG. 12A compares the ratio of staining intensity in cell nuclei to the stain intensity of cytoplasmic and extracellular regions of tissue.
Figure 12B:
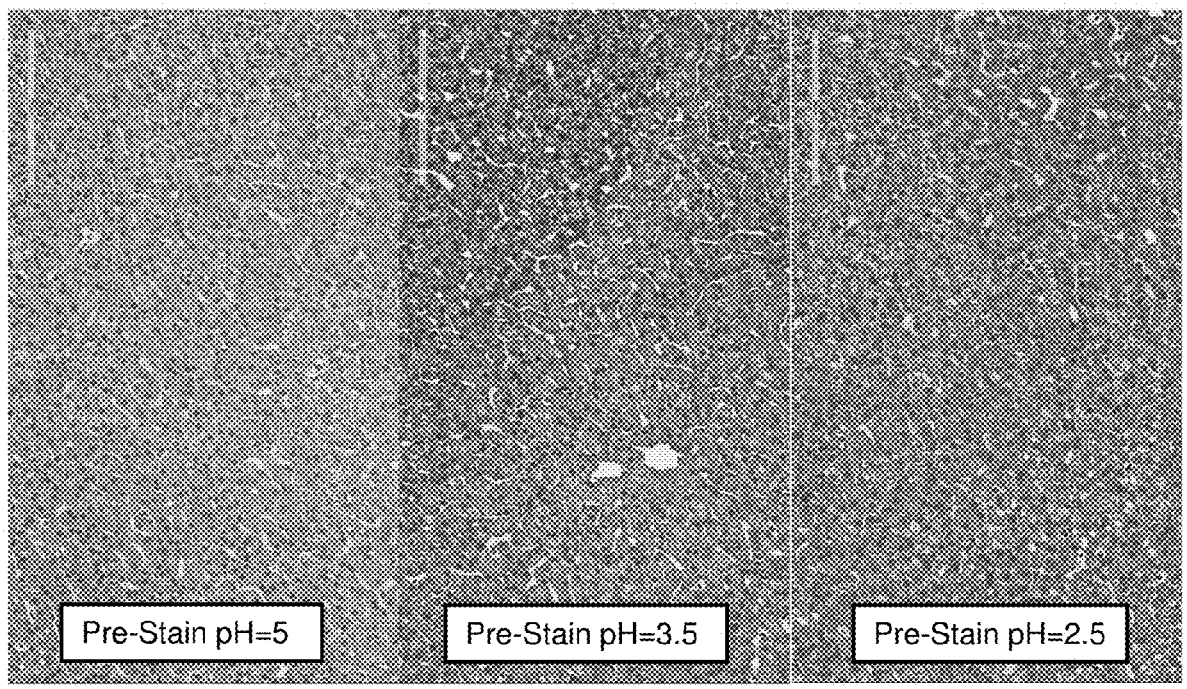
FIG. 12B illustrates the effects of staining at different pHs.

To demonstrate that the reaction conditions inherent to the tissue prior to the printing of staining fluids impact the stain quality for the disclosed staining method, a systematic study of different tissue pH's prior to the printing of hematoxylin was undertaken in 4 µm liver sections mounted on microscope slides. The pH of the tissue section was set by applying 300 µL of a buffer solution to the tissue and then printing hematoxylin and eosin onto the sample using the assay described in Table 8 during the first "Apply Wash (pH wash optional)" step. FIG. 12A compares the ratio of staining intensity in the nuclei to the stain intensity of the cytoplasmic and extracellular regions of tissue. It was hypothesized that the best ratio of these values should represent the optimal staining conditions and that for an increasing pH, overall stain intensity (both specific to the nuclei and non-specific hematoxylin staining should increase). While it was true that staining intensity increased overall as pH increased to a point, at the high end of the scale overall staining intensity decreased (FIG. 12B) to an unacceptable level for a pre-staining buffer with a pH of five. Therefore, the next best condition was selected, a pre-staining buffer with a pH of 3.5. This method could be extended to uniquely adjust the pre-staining tissue buffering conditions for unique tissue types or different staining chemistries and biochemistries.

Table 2 details the capability of a two print head system to deliver a buffering pH solution to a tissue. In one embodiment, the solutions to be dispensed are a weak acid solution and dilute sodium hydroxide. In this case the pH of the dispensed film can be adjusted by adjusting the DPI of the print pattern for each of the fluids. This relates to FIG. 12B where it can be seen that the pH of the tissue prior to printing hematoxylin has an effect on both the stain intensity and stain specificity. This application of inkjet staining is appropriate to meet this need with in-situ mixing the two solutions during print deposition.

TABLE 2

Ratiometric formulations of buffer systems to set the pH of tissue.

| Binary Print Buffer Component 1 | Binary Print Buffer Component 2 | Example Volume ratio (vol 1:vol 2) | Example print ratio (dpi 1:dpi 2) | Target pH | Actual pH |
|---|---|---|---|---|---|
| formic acid, 189 mM | NaOH, 31 mM | 1:1 | 500 dpi:500 dpi | 3 | 3.002 |
| formic acid, 189 mM | NaOH, 31 mM | 1:2 | 460 dpi:650 dpi | 3.5 | 3.496 |
| formic acid, 189 mM | NaOH, 31 mM | 1:3 | 370 dpi:640 dpi | 4 | 4.086 |
| acetic acid, 34.8 mM | NaOH, 38.8 mM | 1:1 | 500 dpi:500 dpi | 4 | 4.094 |
| acetic acid, 34.8 mM | NaOH, 38.8 mM | 10:17 | 460 dpi:600 dpi | 4.5 | 4.500 |
| acetic acid, 34.8 mM | NaOH, 38.8 mM | 10:23 | 400 dpi:607dpi | 5 | 5.083 |

Primary Stain Reagent Compositions

In the context of a primary stain reagent composition, the composition comprises a dye, a stain, or a "primary stain" (as that term is defined here), a viscosity modifying agent, and a surface tension modifying agent. While certain embodiments or examples herein may refer to a primary stain composition comprising hematoxylin or eosin, the skilled artisan will appreciate that primary stain reagent compositions are not limited to these particular dyes and that other dyes, stains, "primary stains," or agents that otherwise enhance the visible contrast of biological structures in a tissue sample may be formulated in a like manner without limitation.

In some embodiments, the amount of viscosity modifying agent ranges from about 35% to about 60% by total weight of the primary stain reagent composition. In other embodiments, the amount of viscosity modifying agent ranges from about 25% to about 75% by total weight of the primary stain reagent composition. In some embodiments, where a dissolved solid is included (e.g. PEG), the amount of viscosity modifying agent may range from about 2% to about 60% by total weight of the primary stain reagent composition. In other embodiments, where a dissolved solid is included, the amount of viscosity modifying agent may range from about 0.1% to about 2% by total weight of the primary stain reagent composition.

In some embodiments, an amount of surface tension modifying agent ranges from about 0.01% to about 0.5% by total weight of the primary stain reagent composition. In other embodiments, an amount of surface tension modifying agent ranges from about 0.001% to about 1% by total weight of the primary stain reagent composition In some embodiments, primary stain reagent composition has a viscosity of 1 cp to about 40 cp. In other embodiments, primary stain reagent composition has a viscosity of 6 cp to about 10 cp. In some embodiments, the primary stain reagent composition has a surface tension up to about 70 dyne/cm. In other embodiments, the primary stain reagent composition has a surface tension of about 25 dyne/cm to about 45 dyne/cm.

In some embodiments, the primary stain reagent solution further comprises one or more stabilizers and/or buffering agents. In some embodiments, the stabilizers include Aluminum Chloride, Aluminum Sulfate. In some embodiments, the buffering agents include Acetate, carbonate, phosphate, Tris-HCl, acetic acid, tris buffer, and phosphate buffer. In general, an amount of stabilizers included within any primary stain reagent composition ranges from about 1% to about 20% by total weight of the primary reagent stain composition. Likewise, an amount of buffers included within any primary stain reagent composition ranges from about 0.5% to about 5% by total weight of the primary reagent stain composition.

Large Molecule Reagent Compositions

In some embodiments, a large molecule reagent composition comprises a biological molecule (e.g. an antibody, an antibody conjugate, an enzyme, a multimer, etc.), a viscosity modifying agent, and a surface tension modifying agent. In some embodiments, the large molecule reagent composition further comprises one or more carrier proteins (e.g. bovine serum albumin, normal goat serum). In some embodiments, the large molecule reagent composition further comprises a buffering agent and/or a preservative composition. In some embodiments, the large molecule reagent composition has a viscosity ranging up to about 15 cp. In other embodiments, the large molecule reagent composition has a viscosity ranging from about 4 cp to about 11 cp. In yet embodiments, the large molecule reagent composition has a viscosity ranging from about 4 cp to about 7 cp. In some embodiments, the large molecule reagent composition has a surface tension ranging from about 20 dyne/cm to about 40 dyne/cm. In other embodiments, the large molecule reagent composition has a surface tension ranging from about 25 dyne/cm to about 35 dyne/cm.

In some embodiments, an amount of viscosity modifying agent ranges from about 1% to about 50% by total weight of the large molecule reagent composition. In other embodiments, an amount of viscosity modifying agent ranges from about 25% to about 75% by total weight of the large molecule reagent composition. In some embodiments, an amount of surface tension modifying agent ranges from about 0.01% to about 0.5% by total weight of the large molecule reagent composition. In other embodiments, an amount of surface tension modifying agent ranges up to about 1% by total weight of the large molecule reagent composition. The skilled artisan will recognize that any included carrier proteins and/or the primary antibody itself may have an effect on surface tension and, in some embodiments, may contribute to a reduction of the surface tension. The skilled artisan will be able to take this factor into account when determining the quantity of any surface tension modifying agent for inclusion within the antibody reagent composition.

Non-limiting examples of antibodies which may be part of any large molecule reagent composition include antibodies specific for cluster of differentiation markers (e.g. CD20, CD3, CD4, CD8, CD45, CD25, CD163 etc.), Ki-67, EGFR, HER2, HPV, ALK, BRAF, OX-40, PD-1, IDL-1, FoxP3, and CTLA-4.

Non-limiting examples of enzymes which may be part of any large molecule reagent composition include horseradish peroxidase, alkaline phosphatase, acid phosphatase, glucose oxidase, $\beta$-galactosidase, $\beta$-glucuronidase or $\beta$-lactamase.

EXAMPLES

The non-limiting examples which follow are intended to further illustrate certain embodiments of the present disclosure.

Example 1

Hematoxylin Formulation

TABLE 3

One embodiment of a hematoxylin formulation.

| INGREDIENTS | Amount (g) | Amount (wt %) | Component Description |
|---|---|---|---|
| DI Water | 152.3 | 57.07 | |
| Propylene Glycol (~40% w/w) | 101.6 | 38.07 | Viscosity Modifier |
| Hematoxylin Dye | 2.27 | 0.85 | Primary Stain |
| Sodium Iodate | 0.24 | 0.09 | Oxidizer |
| Aluminum Chloride Hexahydrate | 2.56 | 0.96 | Stabilizer |
| Aluminum Sulfate Hexadecahydrate | 6.67 | 2.50 | Stabilizer |
| Tomadol 900 (5 uL/mL, 0.98 g/mL) | 1.225 | 0.46 | non-ionic surfactant |
| | 266.865 | 100.00 | |

The composition of Example 1 was found to be sufficient for dispersion by the disclosed piezoelectric deposition method. The final pH of the composition was about 2.22; the surface tension was about 30 dyne/cm; and the viscosity was about 5 cp.

In the case of hematoxylin for inkjet dispensing, several mitigations were discovered to improve the reliability and robustness of the droplet formation process for dispensing this particular stain. First, the inclusion of Aluminum Chloride in the formulation improved the overall stability of the formulation against spontaneous aggregation and precipitation due to insolubility of long-chain metal-ion complexes.

Second, the large fraction of propylene glycol reduced dry out of the hematoxylin formulation when exposed to air by lowering the vapor pressure of the mixture as compared to formulations with a higher water fraction. Both of these improvements represented non-standard (or non-traditional) formulation characteristics targeted at creating a hematoxylin formulation uniquely suited to the inkjet form-factor.

Common to the field of functional printing with inkjet technology is the need to flush significant volumes of ink through a print head to prime the system after use with another fluid. This stems from the design of print head systems fed through multiple ink reservoirs and the resulting large dead volumes. In some designs, this can account for greater than 20% loss in ink. Likewise, the VENTANA HE 600 system has a shared reagent manifold and during the purge/prime cycles, over 30% of the total assay volume is consumed. In the disclosed concept for an inkjet dispensing apparatus, Applicants utilized a cartridge-based inkjet system to overcome these limitations. By preparing complementary formulations of reagents unique to and customized for the printing system, many sources of nozzle fouling (i.e. failure to dispense droplets) were mitigated. However, it was also demonstrated that a prime cycle of 5 µL or less per day was adequate to maintain reliable dispense integrity throughout the daily use of an inkjet reagent cartridge and over for the entire life of the reagent inkjet cartridge.

Example 2

Antibody Formulation

TABLE 4

One embodiment of an antibody formulation

| INGREDIENTS (g) | Amount (g) | Amount (% wt) | Component Description |
|---|---|---|---|
| Water | 117.77 | 46.99% | |
| Glycerol | 125 | 49.87% | viscosity modifier |
| Tris HCl | 1.97 | 0.79% | buffer |
| ProClin 300 (1.03 g/ml) | 0.26 | 0.10% | preservative |
| Bovine Serum Albumin, Frac. V | 2.5 | 1.00% | carrier protein |
| Normal Goat Serum | 2.5 | 1.00% | carrier protein |
| Bio-Soft N91-8 (1.020 g/ml) | 0.64 | 0.26% | non-ionic surfactant |
| Sodium Hydroxide | as needed | Variable | pH adjuster |
| Primary Antibody | variable | Variable | active staining component |
| TOTAL | 250.64 | 100.00% | |

The composition of Example 2 was found to be sufficient for dispersion by the disclosed piezoelectric deposition method. The surface tension was about 28 dyne/cm; and the viscosity was about 7 cp.

Example 3

Eosin Formulation

TABLE 5

One embodiment of an eosin formulation

| INGREDIENTS (g) | Amount (g) | Amount (% wt) | Component Description |
|---|---|---|---|
| DI Water | 204.8 | 39.17% | |
| Propylene Glycol (~60% w/w) | 307.5 | 58.81% | viscosity modifier |
| Eosin Y | 3.8143 | 0.73% | dye |
| Glacial Acetic Acid | 5.5 | 1.05% | pH adjuster |
| Tomadol 900 (2.5 uL/mL, 0.98 g/mL) | 1.274 | 0.24% | non-ionic surfactant |
| | 522.8883 | 100.00% | |

The composition of Example 3 was found to be sufficient for dispersion by the disclosed piezoelectric deposition method. The final pH of the composition was about 4.299; the surface tension was about 41 dyne/cm; the density was 1.042 g/mL; and the viscosity was about 8.1 cp.

Example 4

An Enzyme/Multimer Detection Formulation

Table 5 sets forth an embodiment of an enzyme/or multimer detection formulation. In this particular non-limiting embodiment, the active staining component is Mouse anti-hydroquinone horseradish peroxidase (anti-HQ HRP).

TABLE 6

One embodiment of an Enzyme/Multimer Detection Formulation

| Ingredients | Amount (g) | Amount (% wt) | Component Description |
|---|---|---|---|
| Deionized Water | 50 | 49.25% | |
| Propylene Glycol (1.04 g/ml) | 50 | 49.25% | Viscosity Modifier |
| Potassium Phosphate dibasic | 0.8785 | 0.87% | Buffer |
| Sodium Phosphate Monobasic | 0.138 | 0.14% | Buffer |
| Sodium Chloride | 0.16 | 0.16% | Buffer |
| Liquid Brij, 30% | 0.086 | 0.08% | Surfactant |
| Goat Globulins | 0.15 | 0.15% | Carrier Protein |
| B5 Blocker | 0.068206 | 0.07% | Blocker, non-specific binding |
| ProClin 300 (1.03 g/ml) | 0.02575 | 0.03% | Preservative |
| 6N HCl/6N NaOH | as needed | as needed | pH adjuster |
| Mouse anti-HQ HRP | 0.025 | 0.025% | Active Staining Component (Enzyme-mediated detection) |
| Total | 101.531456 | 100.00% | |

Example 5

An Alternative Antibody Formulation with a Large Molecular Weight Viscosity Modifier An alternative antibody formulation in accordance with the present disclosure is set forth in Table 7.

TABLE 7

An alternative antibody formulation.

| Ingredients | Amount (g) | Amount (% wt) | Component Description |
|---|---|---|---|
| Deionized Water | 54.274 | 54.27% | |
| Glycerol | 40 | 40.00% | Viscosity Modifier |
| Dextran (avg MW 450 kD) | 2 | 2.00% | Viscosity Modifier |
| Tris HCl | 0.95 | 0.95% | Buffer |
| Bovine Serum Albumin, Frac. V | 1.2 | 1.20% | Carrier Protein |
| Normal Goat Serum | 1.2 | 1.20% | Carrier Protein |
| Bio-Soft N91-8 (1.020 g/ml) | 0.256 | 0.26% | Surfactant |
| ProClin 300 (1.03 g/ml) | 0.12 | 0.12% | Preservative |
| 6N NaOH | as needed | as needed | pH adjuster |
| Primary Antibody | variable | variable | Active Staining Component |
| Total | 100 | 100.00% | |

Example 6

Comparison of a Traditional Staining Procedure to an Inkjet Deposition Staining Procedure Set forth herein is a comparison of example assays from a conventional single-slide staining (Table 9) system and the droplet-on-demand dispensing means described in this disclosure (Table 8). Both assay tables assume an offline deparaffinization process as well as a manual workup to coverslipping after the assay is complete. While the VENTANA HE 600 assay for H&E staining (representing a conventional single slide staining apparatus) may be "dialed-in" to adjust the staining using incubation times only, the Inkjet Staining process offers several adjustment point unique to a droplet deposition (i.e. inkjet) staining process. First, staining is fundamentally mass-limited, as shown in FIGS. 4A and 5B, while a primary driver for stain intensity on conventional staining system is incubation time. In fact, this is the only customer-facing feature to "dial" the assay intensity and specificity in the example of a conventional staining apparatus.

TABLE 8

Inkjet Staining Assay Script

| Assay Step | Volume (μl) | Fluid Process | Process Time (min) | Active Time (min) | Notes |
|---|---|---|---|---|---|
| Set Slide Temperature, 40 C. | — | | — | — | Staining intensity may be adjusted using assay temperature |
| HW Initialization | — | | 0.6 | 0 | From slide "park" to pH wash (first location, includes height Z adjust for print heads) |
| Apply pH Wash | 300 | bulk, on tissue | 0 | 0 | Background/non-specific staining is mitigated by "setting" the tissue pH prior to printing hematoxylin |
| Remove Fluid | — | | 0.180 | 0.100 | removes fluid down to ~5 uL |
| Print Hematoxylin | 2.5 | 1000 × 1000 print, 10 pL/drop | 1.580 | 1.580 | |
| Incubation | — | | 1.000 | 1.000 | Incubation steps are optional to drive stain intensity |
| Print Hematoxylin | 2.5 | 1000 × 1000 print, 10 pL/drop | 1.580 | 1.580 | |
| Incubation | — | | 1.000 | 1.000 | |
| Print Hematoxylin | 2.5 | 1000 × 1000 print, 10 pL/drop | 1.580 | 1.580 | Staining intensity may be adjusted by printing onto the tissue multiple times |
| Incubation | — | | 1.000 | 1.000 | |
| Apply Wash (pH wash optional) | 300 | bulk, on tissue | 0.033 | 0.033 | Removes unbound hematoxylin prior to bluing. May "clean up" background staining |
| Incubation | — | | 1.000 | 1.000 | Optional "soaking" step to homogenize the stain across the tissue |
| Remove Fluid | — | | 0.180 | 0.100 | |
| Apply Wash | 300 | bulk, on tissue | 0.033 | 0.033 | |

TABLE 8-continued

Inkjet Staining Assay Script

| Assay Step | Volume (μl) | Fluid Process | Process Time (min) | Active Time (min) | Notes |
|---|---|---|---|---|---|
| Incubation | — | | 1.000 | 1.000 | |
| Remove Fluid | | | 0.180 | 0.100 | |
| Apply Bluing | 300 | bulk, on tissue | 0.050 | 0.050 | pH adjustment to basic conditions, locks the specific staining of hematoxylin onto the tissue |
| Incubation | — | | 0.500 | 0.500 | |
| Apply Wash | 300 | bulk, on tissue | 0.130 | 0.033 | Remove excess bluing. Option to adjust pH to dial eosin intensity |
| Remove Fluid | | | 0.180 | 0.100 | |
| Apply Wash (pH wash optional) | 300 | bulk, on tissue | 0.033 | 0.033 | |
| Remove Fluid | | | 0.180 | 0.100 | |
| Print Eosin | 2.5 | 1000 × 1000 print, 10 pL/drop | 1.580 | 1.580 | May be made ultra-bright by managing pH prior to application. No incubation necessary |
| Apply Wash | 300 | bulk, on tissue | 0.033 | 0.033 | Differentiation of eosin into three shades (RBCs, |
| Remove Fluid | | | 0.180 | 0.100 | |
| Apply Wash | 300 | bulk, on tissue | 0.033 | 0.033 | Removal of excess eosin |
| Remove Fluid | | | 0.180 | 0.100 | |
| Apply Wash | 300 | bulk, on tissue | 0.033 | 0.033 | |
| Remove Fluid | | | 0.180 | 0.100 | |

However, on the inkjet staining system the primary drivers for dialing stain intensity are the number of print passes and the DPI (drop per inch) or density of the print area, both of which adjust the total mass of staining material deposited. In FIG. 4A, the hematoxylin intensity is driven up by increasing the number of print passes on the tissue and likewise in FIG. 5A, the eosin intensity is similarly driven up by the deposition of additional print layers on the tissue. As shown in Table 8, for one embodiment of the disclosed staining process, the assay time is fixed (due to the "dialability" of stain intensity with mass deposition), as opposed to variable for the conventional process (due to the "dialability" of stain intensity being driven by incubation time). Further there is a significant reduction in the amount of liquid waste generated, from about 14.24 mL for the convention process down to about 2.71 mL for an embodiment of the inkjet staining process. This result highlights the assay volume miniaturization effect possible with an inkjet deposition system, as suggested in Table 10.

TABLE 9

Conventional staining apparatus assay script

| Assay Step | Volume (uL) | Fluid Process | Process Time (min) | Notes |
|---|---|---|---|---|
| Set Stainer Air Temperature, 45 C. | — | | — | Fixed temperature control in conventional system |
| Wash, Incubate, Remove Fluid | 1000.00 | Bulk | 0.333 | |
| Wash, Incubate, Remove Fluid | 1000.00 | Bulk | 0.333 | |
| Hematoxylin, Incubate, Remove Fluid | 1350.00 | Bulk | variable, 1-10 | Stain intensity is driven using incubation time, which may be between one and ten minutes |
| Wash, Incubate, Remove Fluid | 1000.00 | Bulk | 0.667 | |
| Acid Wash, Incubate, Remove Fluid | 1200.00 | Bulk | variable, 0-3 | Specific staining is driven using acid wash incubation time, which is variable and also decreases stain intensity |

TABLE 9-continued

Conventional staining apparatus assay script

| Assay Step | Volume (uL) | Fluid Process | Process Time (min) | Notes |
|---|---|---|---|---|
| Wash, Incubate, Remove Fluid | 900.00 | Bulk | 0.333 | |
| Bluing, Incubate, Remove Fluid | 1050.00 | Bulk | 0.500 | |
| Wash, Incubate, Remove Fluid | 900.00 | Bulk | 0.333 | |
| Eosin, Incubate, Remove Fluid | 1350.00 | Bulk | variable, 0.5-7 | |
| Wash, Incubate, Remove Fluid | 1000.00 | Bulk | 0.333 | |
| Wash | 1000.00 | Bulk | 0.333 | |
| Wash | 1000.00 | Bulk | 1.333 | |
| Purge/Prime Steps Between Fluids Total (Hematoxylin) | 1870.61 | — | — | Necessary to change to different fluids on a conventional system |
| Purge/Prime Steps Between Fluids Total (Wash) | 2100.99 | — | — | Necessary to change to different fluids on a conventional system |
| Purge/Prime Steps Between Fluids Total (Acid Wash) | 650.14 | — | — | Necessary to change to different fluids on a conventional system |
| Purge/Prime Steps Between Fluids Total (Bluing) | 579.99 | — | — | Necessary to change to different fluids on the conventional system |
| Purge/Prime Steps Between Fluids Total (Eosin) | 610.78 | — | — | Necessary to change to different fluids on a conventional |

Table 10 which follows illustrates an inkjet deposition process according to embodiments of the present disclosure. As compared with the VENTANA HE 600 process, for the inkjet staining system the primary drivers for dialing stain intensity are the number of print passes and the DPI (drop per inch) or density of the print area, both of which adjust the total mass of staining material deposited. In this particular assay, the total assay volume utilized was about 2.71 mL, and the total assay time was about 14.24 minutes.

TABLE 10

Summary comparison of inkjet and conventional assays

| | Conventional H&E | Inkjet H&E |
|---|---|---|
| Total Staining Assay Time (min) | 6.00 to 24.50 | 14.24 |
| Total Assay Volume (mL) | 19.11 | 2.71 |

While a small incubation period is still a component of some processing steps for staining via the disclosed inkjet deposition processes, the application of an intense eosin stain (for staining the cytoplasm) does not require any additional incubation after the printing. Without wishing to be bound by any particular theory, it is believed that this illustrates that staining is mass-limited when using ultra-low volumes or reagent, as well as the fact that reaction kinetics may be improved (reduction of staining time from seven minutes to one minute) even with a 100-fold reduction in reagent, as compared with traditional staining techniques.

Example 7

Purging and Cleaning

Two common practices in the field of inkjet printing are purging and blotting a print head to induce fluid to flow into the capillary space and prime the nozzles for dispensing. Purging refers to the application of positive pressure within the ink container in order to force jets of fluid out of the nozzles, without actuating the piezoelectric or thermal droplet generation elements. Purging may also be used to remove occlusions (e.g. solid crystals, protein aggregates) and allow the actuation of droplets from the nozzle. Blotting refers to the application of a wicking pad to the outside of the nozzle area of the print head. This induces flow through the nozzles to prime for printing or to clean up any residual fluid on the print head. Both these methods are employed on the current inkjet staining system for managing "well behaved" fluids (i.e. those fluids without a tendency to crystallize and occlude the nozzles).

In investigating inkjet staining, several methods of cleaning and maintaining print heads were discovered using physical or chemical treatment. Generally, physical treatment was the preferred method as it was less destructive and may be automated relatively easily. For the maintenance of print heads, a moist, local high humidity environment was a key factor in preventing crystallization or precipitate formation at the nozzles. By resting a blotting pad filled with a mixture of water and glycol against the nozzle plate during long-term storage on the inkjet staining system, dry out was mitigated.

Two effective solvent systems used for the cleaning of crystalized material from the print heads were 3% periodic acid and a mixture of hydrogen peroxide/Sodium Carbonate. Both were effective at removing occlusions from the print nozzles.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the disclosure herein has been described with reference to particular embodiments, it is to be understood that these embodiments are merely illustrative of the principles and applications of the present disclosure. It is therefore understood that numerous modifications may be made to the illustrative embodiments and that other arrangements may be devised without departing from the spirit and scope of the present disclosure as defined by the appended claims.

The invention claimed is:

1. A method of dispensing a reagent composition to a biological tissue sample disposed on a surface of a microscope slide, comprising:
    identifying one or more regions of the biological tissue sample disposed on the surface of the microscope slide for receiving the reagent composition;
    determining a dispense pattern based on the one or more identified regions;
    depositing a protective fluid layer comprising an immiscible oil onto a surface of the biological tissue sample; and
    dispensing, based on the determined dispense pattern,— between about 360 nL/in$^2$—to about 14.4 µL/in$^2$—of the reagent composition per pass to the biological tissue sample with a piezoelectric deposition system such that the reagent composition penetrates the deposited protective fluid layer and directly contacts the biological tissue sample;
    wherein the reagent composition comprises an antibody.

2. The method of claim 1, wherein the reagent composition is dispensed at a velocity of between about 5 m/s to about 15 m/s.

3. The method of claim 1, wherein a density of the reagent composition is greater than a density of the immiscible oil.

4. The method of claim 1, wherein the reagent composition is dispensed with a kinetic energy which exceeds a surface tension of the deposited protective fluid layer.

5. The method of claim 4, wherein the kinetic energy is greater than $9.52 \times 10^{-10}$ Joules.

6. The method of claim 1, wherein the reagent composition further comprises a surfactant and a viscosity modifier, and wherein the reagent composition has a viscosity ranging from about 4 cp to about 7 cp, and a surface tension ranging from about 20 dyne/cm to about 40 dyne/cm.

7. The method of claim 6, wherein the reagent composition is dispensed at a shear rate of less than about $5 \times 10^5$ s$^{-1}$.

8. The method of claim 6, wherein the reagent composition further comprises a buffer and a carrier protein.

9. The method of claim 8, wherein the reagent composition consists essentially of the primary antibody, the surfactant, the viscosity modifier, the buffer, and the carrier protein.

10. A method of dispensing one or more reagent compositions onto a tissue specimen disposed on a surface of a microscope slide, comprising:
    obtaining an image of the tissue specimen disposed on the surface of the microscope slide;
    identifying one or more regions in the obtained image for receiving the reagent composition;
    dispensing a protective fluid layer comprising an immiscible oil onto the tissue specimen; and
    dispensing the reagent composition to each of the one or more identified regions with a piezoelectric deposition system such that the reagent composition penetrates the protective fluid layer overlaying the tissue specimen and directly contacts the tissue specimen, wherein a cumulative amount of the reagent composition dispensed ranges from about 10 µL/in$^2$ to about 30 µL/in$^2$; and wherein the reagent composition comprises an antibody.

11. The method of claim 10, wherein the antibody is a primary antibody specific to a protein target within the tissue specimen.

12. The method of claim 10, wherein the reagent composition further comprises a surfactant and a viscosity modifier.

13. The method of claim 12, wherein the reagent composition further comprises a buffer and a carrier protein.

* * * * *